United States Patent
Khalil et al.

(10) Patent No.: US 12,310,574 B2
(45) Date of Patent: May 27, 2025

(54) KNOTLESS SUTURE ANCHOR WITH RE-TENSION FEATURES

(71) Applicant: AEVUMED, INC., Malvern, PA (US)

(72) Inventors: Saif Khalil, Malvern, PA (US); Miles Curtis, Philadelphia, PA (US)

(73) Assignee: AEVUMED, INC., Malvern, PA (US)

( * ) Notice: Subject to any disclaimer, the term of this patent is extended or adjusted under 35 U.S.C. 154(b) by 448 days.

(21) Appl. No.: 17/903,443

(22) Filed: Sep. 6, 2022

(65) Prior Publication Data

US 2023/0248351 A1 Aug. 10, 2023

Related U.S. Application Data

(60) Provisional application No. 63/288,126, filed on Dec. 10, 2021, provisional application No. 63/240,561, filed on Sep. 3, 2021.

(51) Int. Cl.
*A61B 17/04* (2006.01)

(52) U.S. Cl.
CPC .. *A61B 17/0401* (2013.01); *A61B 2017/0414* (2013.01); *A61B 2017/044* (2013.01)

(58) Field of Classification Search
CPC ............ A61B 17/0401; A61B 17/0482; A61B 2017/0414; A61B 2017/044; A61B 2017/0046; A61B 2017/00964; A61B 2017/0403; A61B 2017/0409; A61B 2017/0412; A61B 2017/0437; A61B 2017/045; A61B 2017/0453

See application file for complete search history.

(56) References Cited

U.S. PATENT DOCUMENTS

| | | | | |
|---|---|---|---|---|
| 5,702,397 | A * | 12/1997 | Goble | A61F 2/0811 606/86 R |
| 8,961,576 | B2 * | 2/2015 | Hodge | A61B 17/0401 606/328 |
| 9,357,995 | B2 * | 6/2016 | Hodge | A61B 17/8625 |
| 2012/0035671 | A1 * | 2/2012 | Hodge | A61B 17/8685 606/328 |
| 2015/0164499 | A1 * | 6/2015 | Hodge | A61B 17/0401 606/232 |
| 2022/0000470 | A1 * | 1/2022 | Fallin | A61B 17/0401 |
| 2023/0069080 | A1 * | 3/2023 | Rao | A61B 17/0485 |
| 2023/0248351 | A1 * | 8/2023 | Khalil | A61B 17/0401 606/232 |

* cited by examiner

*Primary Examiner* — Ryan J. Severson
(74) *Attorney, Agent, or Firm* — Riverside Law LLP

(57) ABSTRACT

The present invention provides knotless suture anchor systems and devices for attaching soft tissue to bone. The systems and devices include suture anchors configured to engage and fasten sutures using set screws such that the locked sutures are free from frictional engagement with bone, screw threading, or internal walls of the anchors and set screws. Fastened sutures may also be re-tensioned by loosening a set screw to unfasten the sutures, adjusting the positioning of the sutures, and tightening the set screw to refasten the sutures. In some embodiments, the systems and devices enable the insertion of a suture anchor without preloading sutures, such that one or more sutures may be fastened to the suture anchor after implanting the suture anchor into a subject.

46 Claims, 41 Drawing Sheets

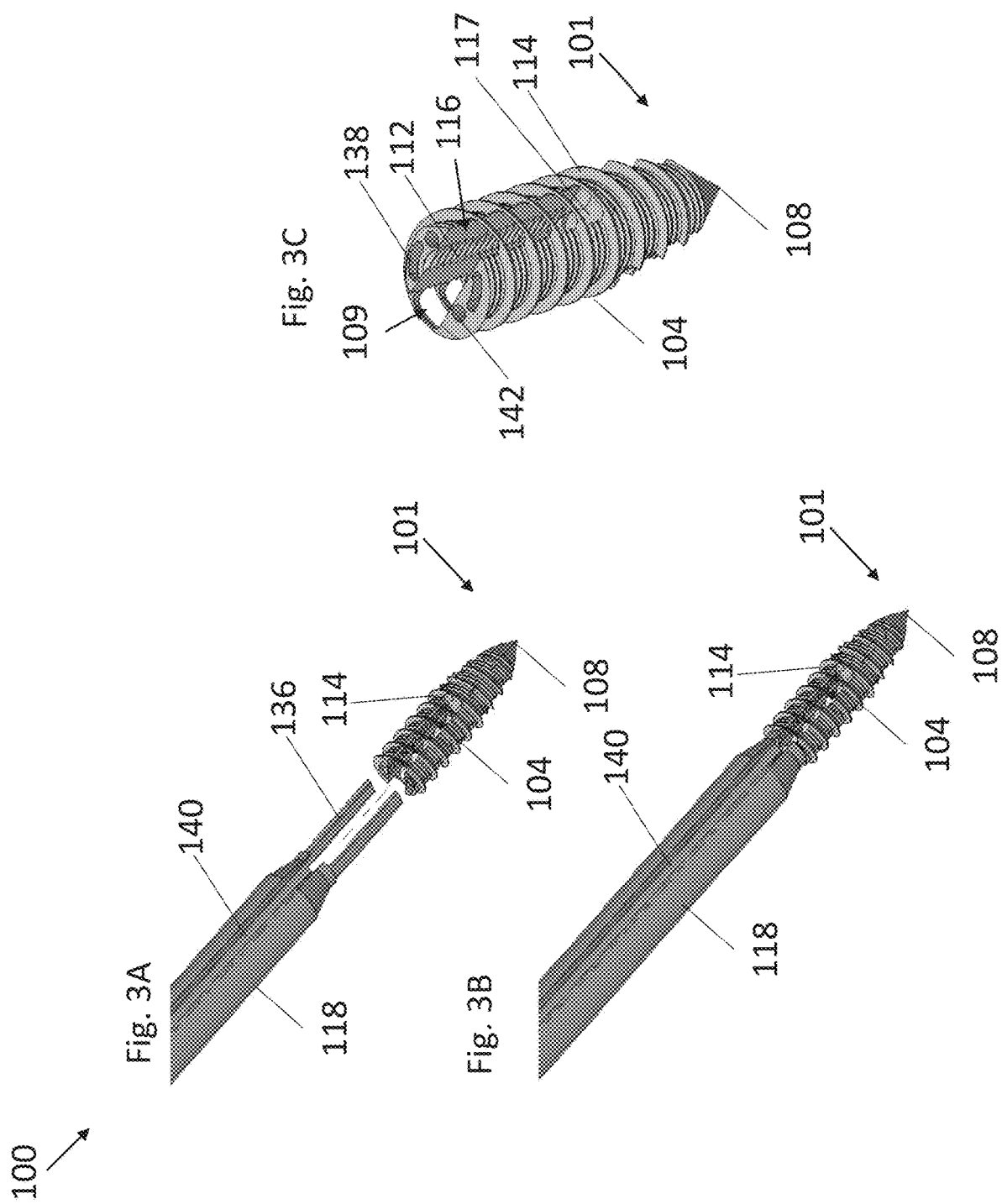

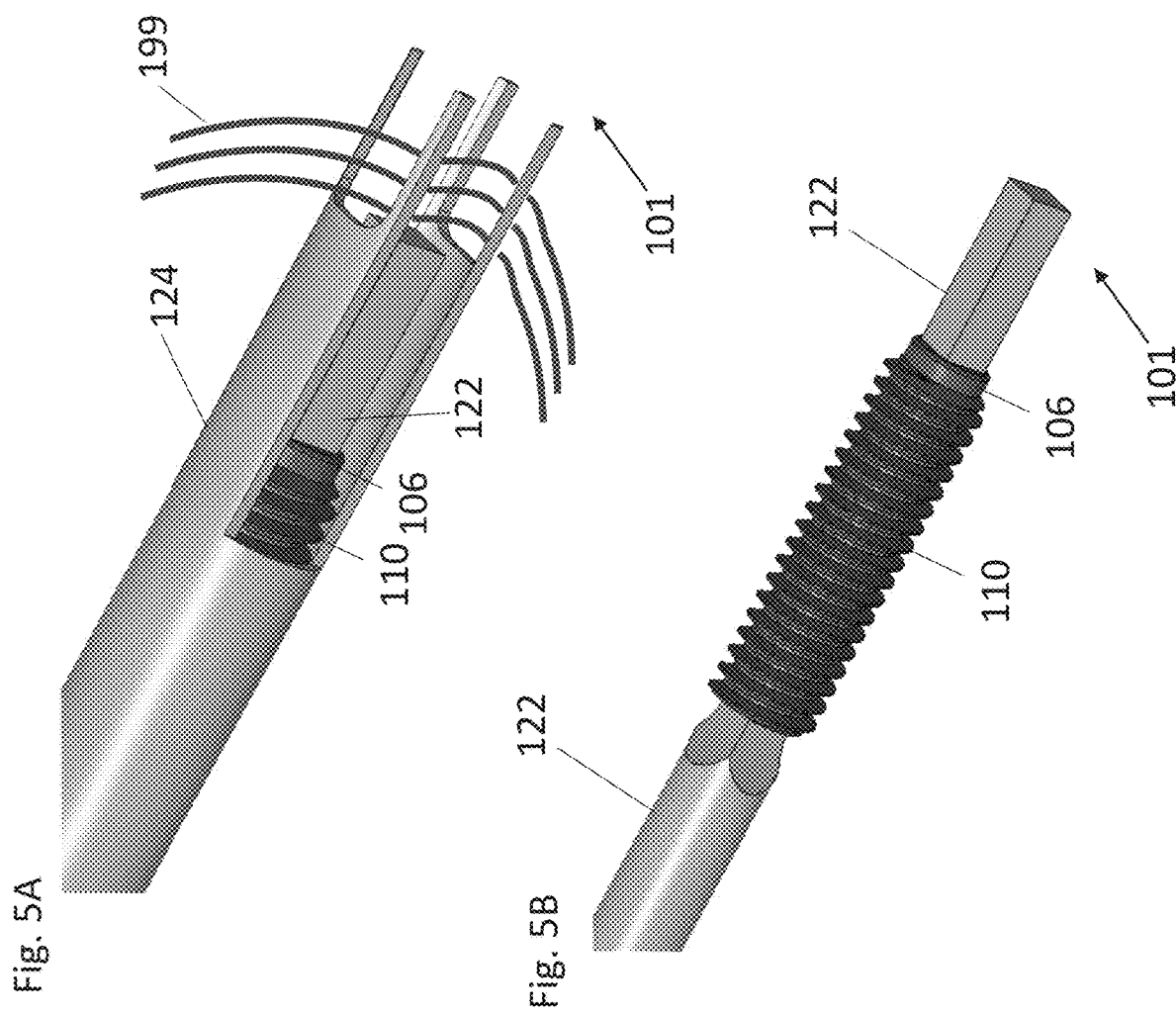

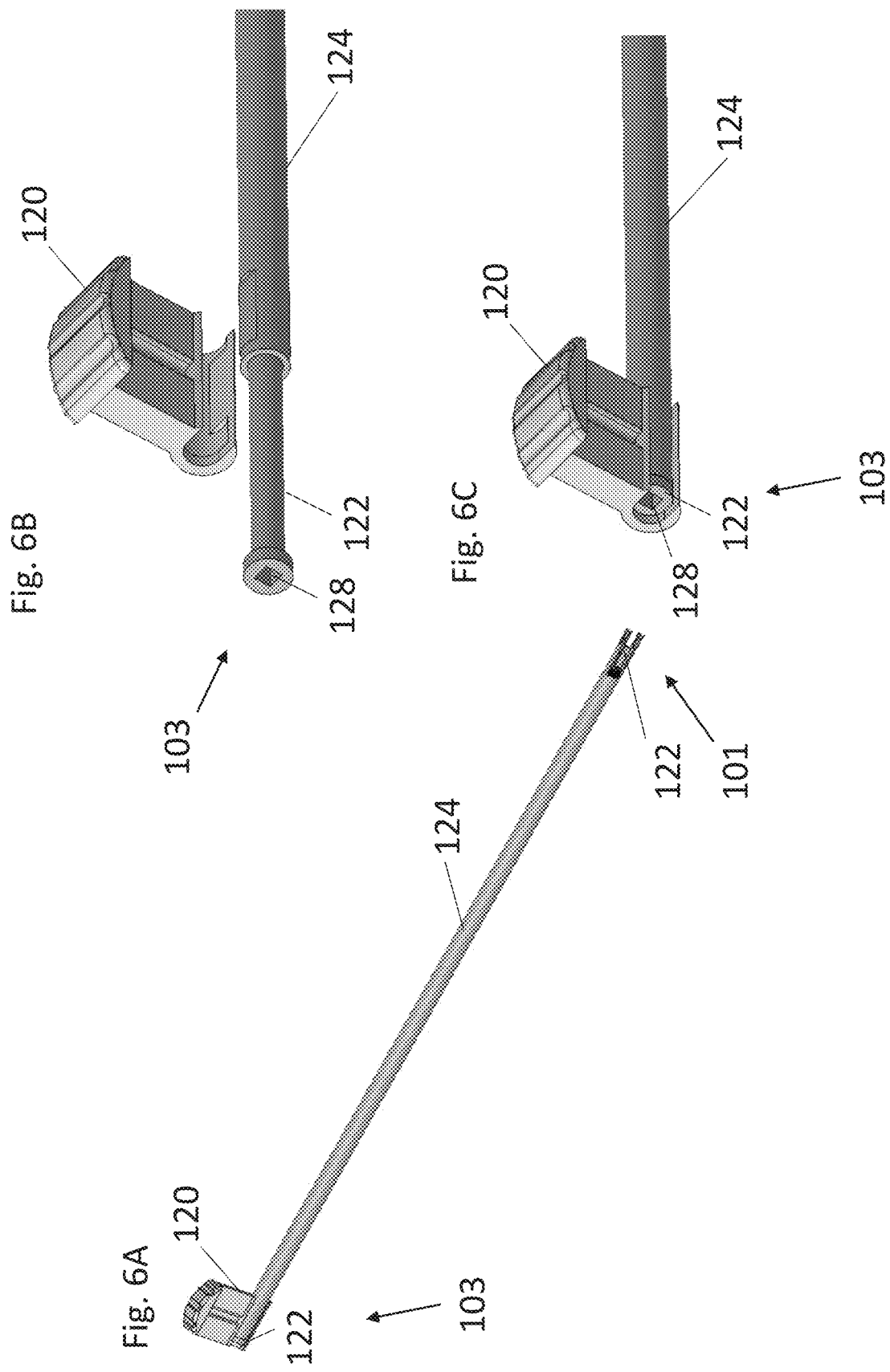

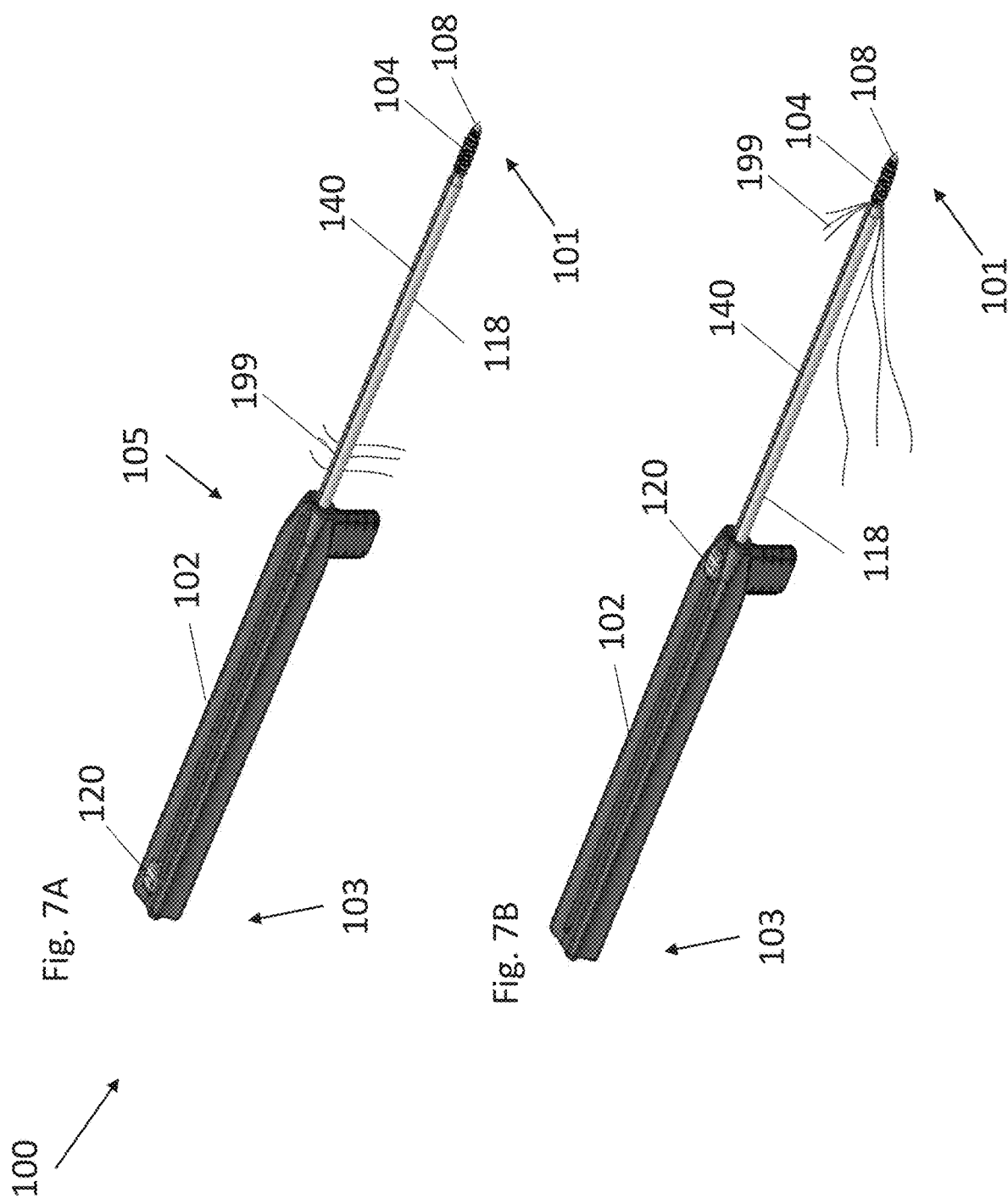

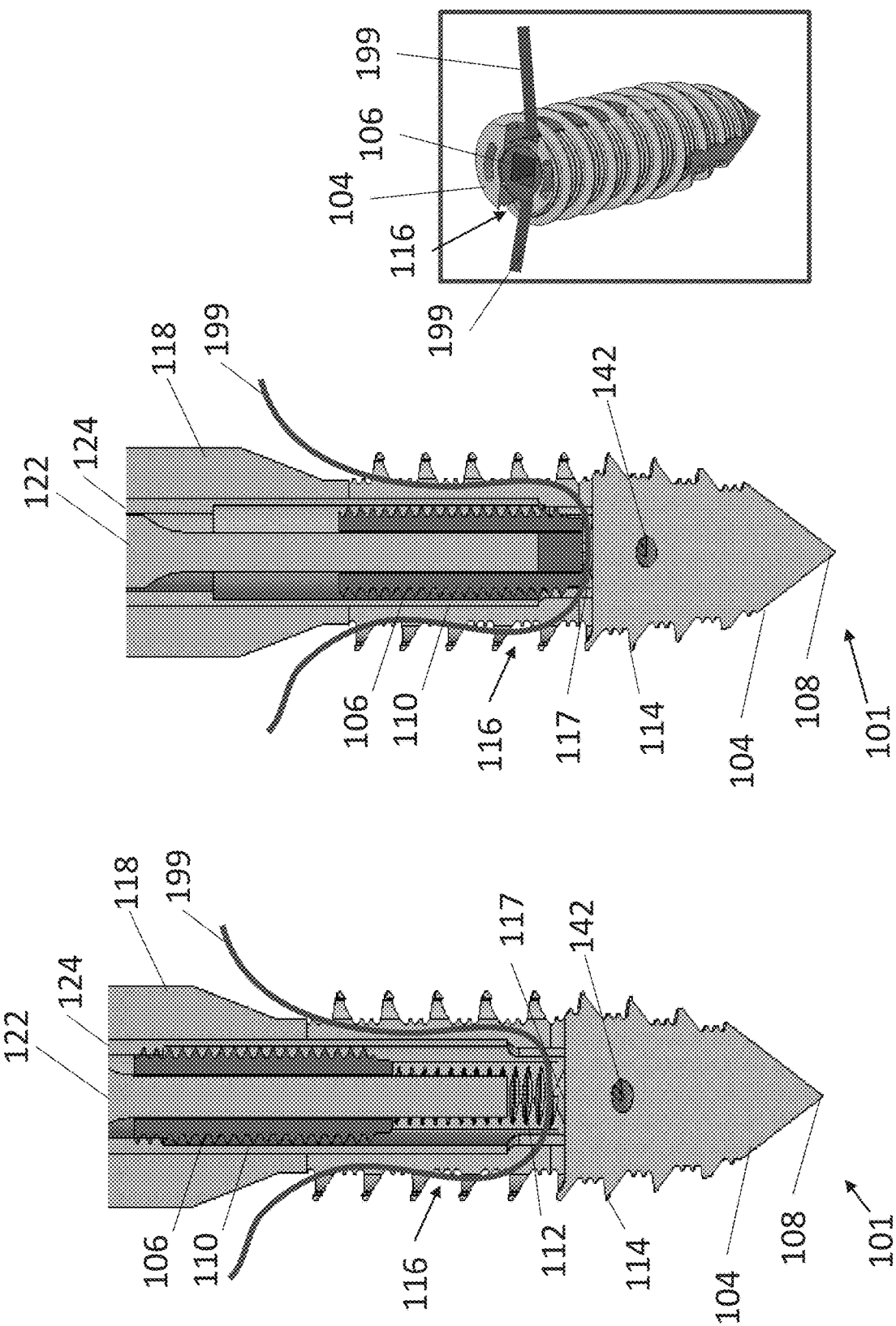

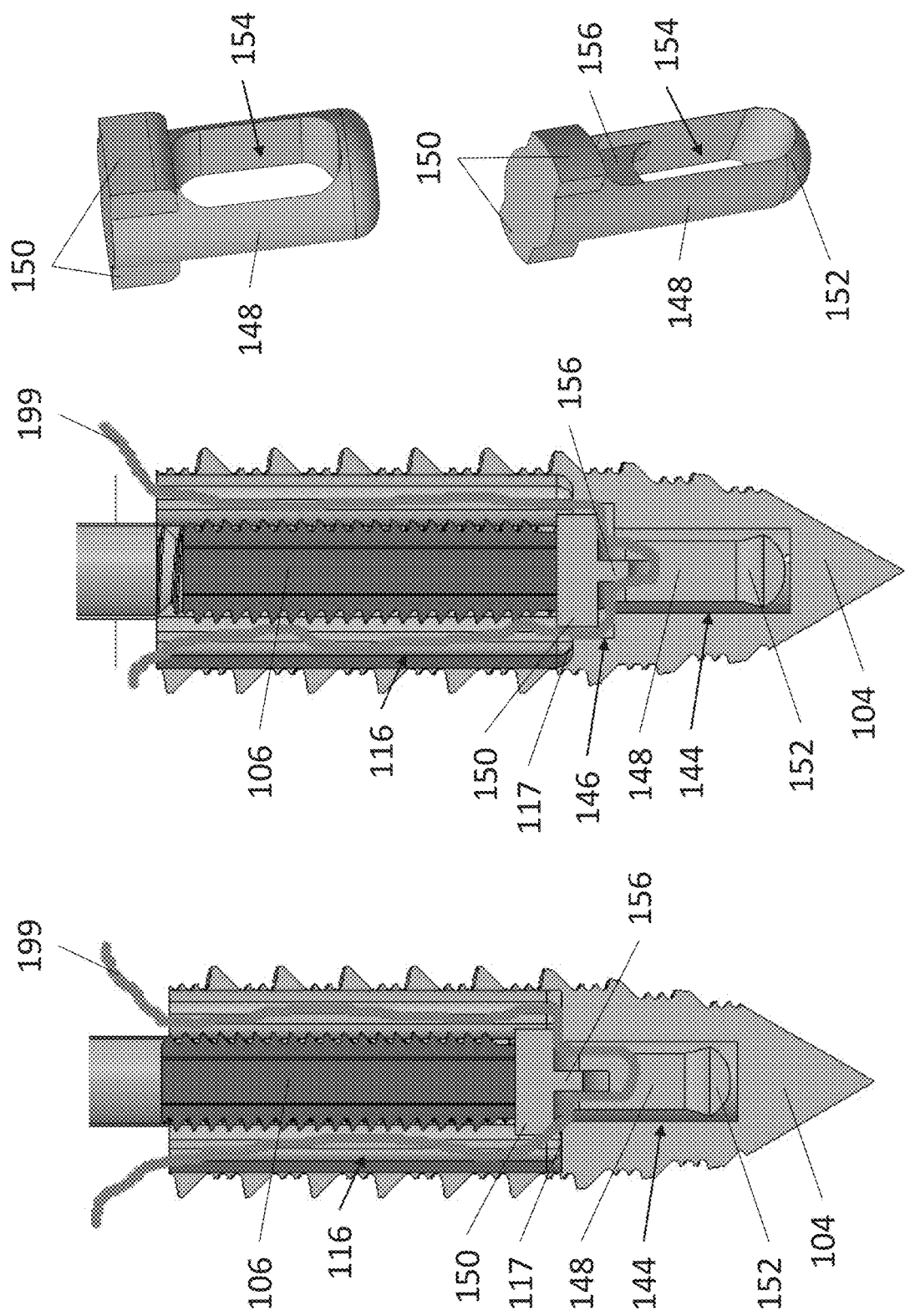

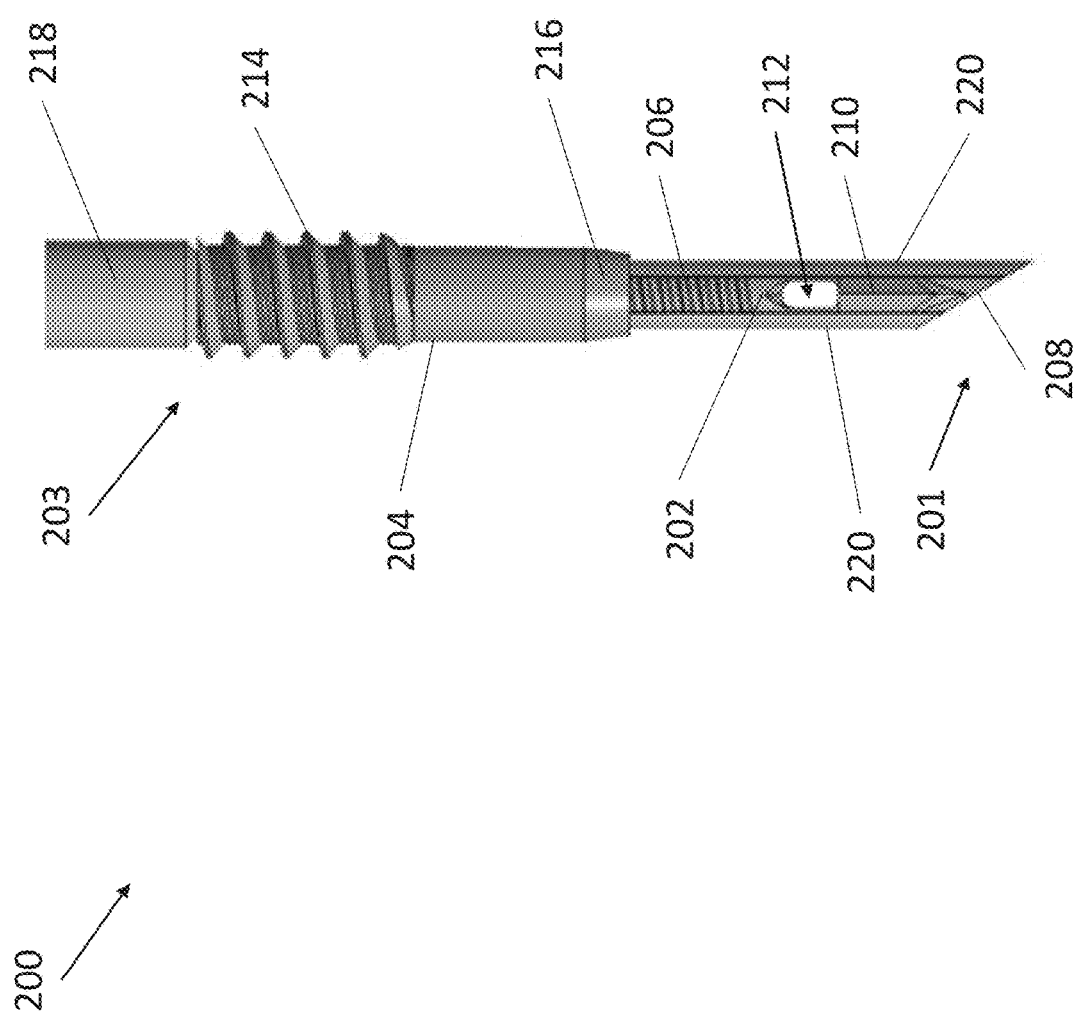

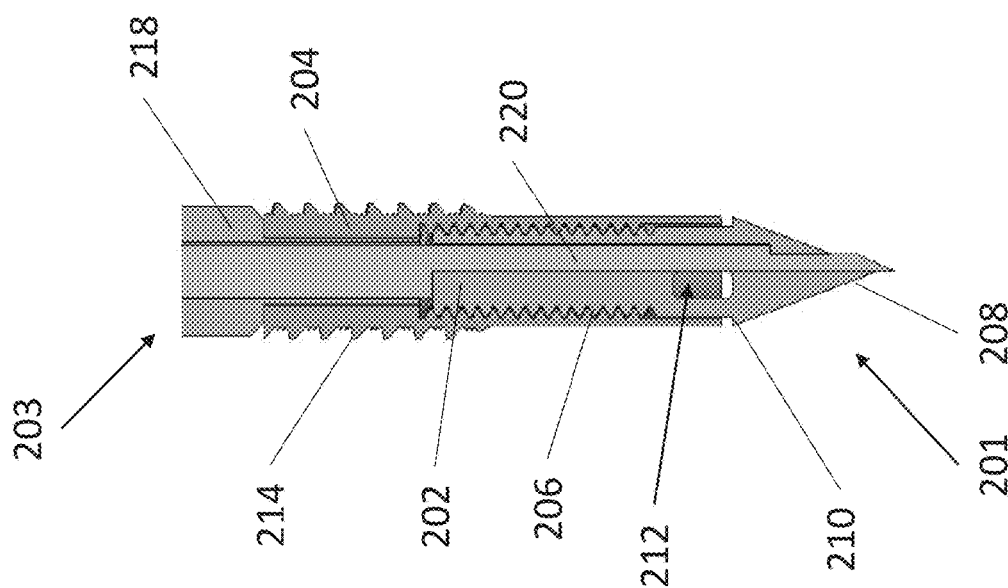
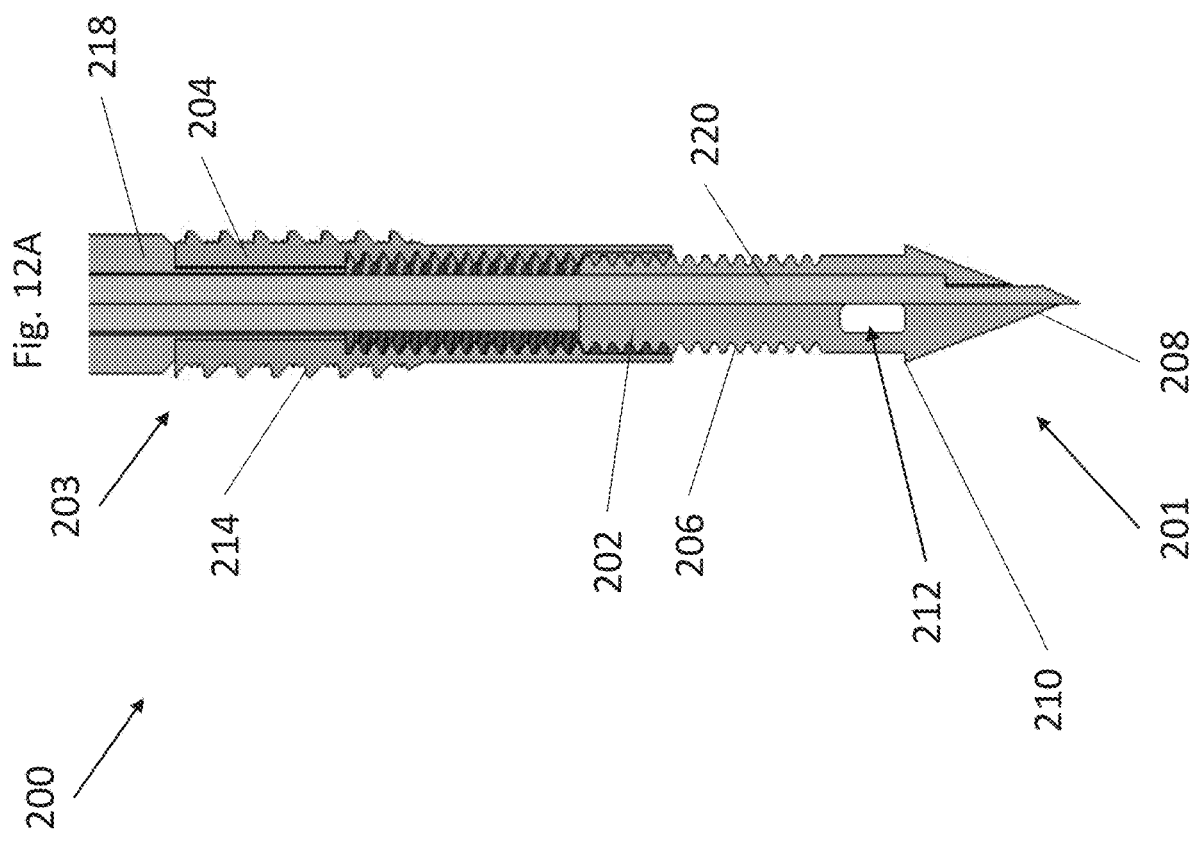

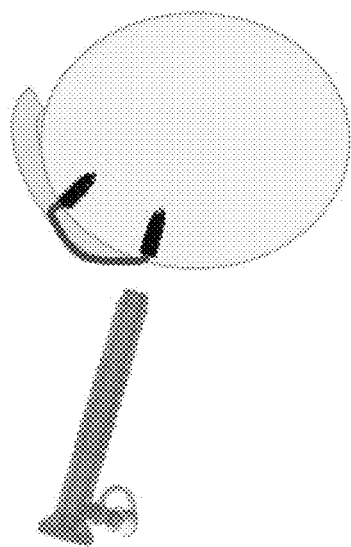
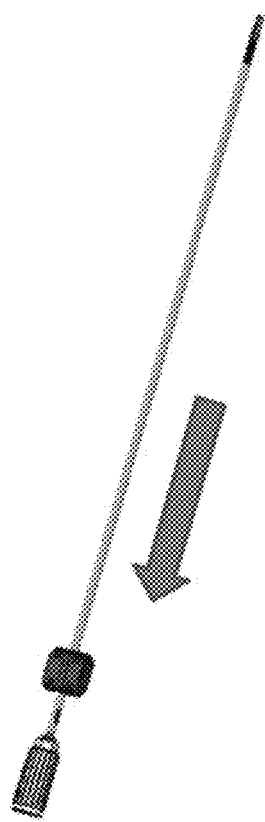
Fig. 22G

KNOTLESS SUTURE ANCHOR WITH RE-TENSION FEATURES

CROSS-REFERENCE TO RELATED APPLICATIONS

This application claims priority to U.S. Provisional Application No. 63/240,561 filed on Sep. 3, 2021, and U.S. Provisional Application No. 63/288,126 filed Dec. 10, 2021, the contents of which are incorporated herein by reference in their entirety.

BACKGROUND OF THE INVENTION

Suture anchors are commonly employed to attach soft tissue such as tendons or ligaments to bone. For instance, in a rotator cuff repair, suture is passed through a detached or damaged portion of a rotator cuff tendon. A suture anchor is implanted into the adjacent bone. By attaching the suture to the anchor, the tendon is pulled into contact with the bone to promote adhesion of the tendon to the bone. Such procedures are often performed arthroscopically through a narrow cannula. This reduces trauma to the patient but makes attachment of the suture to the anchor using a knot more difficult. Knotless suture anchors may be employed which allow a surgeon to affix a suture from another anchor without having to tie a knot. Existing knotless suture anchors pre-tension a suture to a desired degree prior to securing the suture by trapping it between outer threading of the knotless suture anchor and adjacent bone. As the knotless suture anchor is screwed in, the tension in the suture may be loosened or overtightened with no means to re-tension the suture other than removing the knotless suture anchor. The suture may also interfere with the engagement between the knotless suture anchor threading and adjacent bone, leading to poor fit, compromised healing or resorption, and possibly anchor or suture pullout.

Thus, there is a need in the art for improved knotless suture anchors allow sutures to be re-tensioned, as well as knotless suture anchors that enhance repair and healing by securing sutures without trapping the sutures against bone. The present invention meets this need.

SUMMARY OF THE INVENTION

In one aspect, the present invention relates to a knotless suture anchor device comprising: a suture anchor comprising an elongate cylindrical body having a proximal end and a distal end, and a suture channel extending from an opening at the proximal end to a distal suture channel face, wherein the suture channel comprises an oblong cross-sectional shape; and a set screw comprising an elongate tubular body having a proximal end and a distal end, a screw thread positioned on an outer surface of the tubular body, wherein the set screw is configured to screw into the suture channel to form opposing lateral spaces in the suture channel.

In one embodiment, the set screw and the suture anchor are configured to reversibly fasten one or more lengths of suture thread within the suture channel such that the one or more lengths of suture thread are pinched only between the distal end of the set screw and the distal suture channel face while remaining free from engagement with threading or walls of the suture channel.

In one embodiment, the suture channel comprises opposing partial threading mated to the screw thread of the set screw. In one embodiment, the suture anchor comprises a distal piercing tip having a shape selected from the group consisting of: a conical tip, a pyramidal tip, a hypodermic needle tip, a wedge tip, a bladed tip, and a trocar tip. In one embodiment, the suture anchor is fabricated from a material selected from the group consisting of: PEEK, PAEK, PEKK, titanium, titanium-alloys, bioabsorbables, platinum, plastic, metal, and combinations thereof.

In one embodiment, the suture anchor is engageable to a distal end of an outer driver of an anchor driver and the set screw is engageable to a distal end of an inner set screw driver of the anchor driver positioned within a lumen of the outer driver. In one embodiment, the outer driver and the inner set screw driver each rotate about a longitudinal axis of the anchor driver, and the inner set screw driver rotates independently from the outer driver. In one embodiment, the inner set screw driver is rotatably connected to and telescopes from a drive shaft that is rotatably connected to a proximal end of the anchor driver. In one embodiment, the outer driver comprises opposing longitudinal suture slots configured to receive one or more lengths of suture thread. In one embodiment, the outer driver further comprises a releasably engaged suture blocking sleeve comprising a tube-like shape having a central lumen with an open lateral side, such that the suture blocking sleeve is rotatable to cover and expose one or more of the opposing longitudinal suture slots. In one embodiment, the inner set screw driver is configured to push one or more lengths of suture thread received through the opposing longitudinal suture slots into the suture anchor.

In one embodiment, the anchor device further comprises a substantially cylindrical eyelet shuttle having an eyelet configured to receive a suture therethrough, wherein the eyelet shuttle is configured to fit within a shuttle slot formed within the distal suture channel face. In one embodiment, the eyelet shuttle comprises an interference rib extending from a proximal end of the eyelet in a distal direction. In one embodiment, the eyelet shuttle comprises laterally extending proximal tabs configured to reversibly fasten one or more lengths of suture thread within the suture channel such that the one or more lengths of suture thread are pinched only between the proximal tabs and the distal suture channel face while remaining free from engagement with threading or walls of the suture channel. In one embodiment, the distal suture channel face comprises a tab slot formed adjacent to the shuttle slot configured to reversibly fasten one or more lengths of suture thread within the suture channel such that the one or more lengths of suture thread are pinched only between the proximal tabs and distal and lateral faces of the tab slot while remaining free from engagement with threading or walls of the suture channel.

In one embodiment, the suture anchor comprises a threaded exterior. In one embodiment, the suture anchor comprises a ribbed exterior configured for push-in insertion. In one embodiment, the suture anchor comprises an exterior having a plurality of flexing flaps configured for push-in insertion, wherein each flexing flap extends out of the cylindrical body and is angled towards the proximal end of the cylindrical body.

In one aspect, the present invention relates to a method of attaching soft tissue to bone, the method comprising the steps of: providing a knotless suture anchor device having a suture channel extending from a proximal opening to a distal suture channel face, the suture channel having an oblong cross-sectional shape; driving the suture anchor into a bone of a subject; providing a set screw having a threaded tubular shape sized to fit within the suture channel of the suture anchor, the set screw having a circular cross-sectional shape; pushing at least one suture thread into the proximal opening of the suture channel with a distal end of the set screw; and driving the set screw into the suture channel such that the at least one suture thread is securely pinched only between the distal end of the set screw and the distal suture channel face and is free from engagement with threading or walls of the suture channel.

In one embodiment, the knotless suture anchor is driven into a preformed hole in a bone of a subject. In one embodiment, the hole is formed using a tool selected from the group consisting of: an awl, a tap, and a drill. In one embodiment, the knotless suture anchor is punched or hammered directly into a bone of a subject without a preformed hole. In one embodiment, the at least one suture thread is re-tensioned by partially driving the set screw out of the suture channel to free the at least one suture from the distal end of the set screw and the distal suture channel face. In one embodiment, a remainder of each of the at least one suture thread is positioned in lateral spaces of the suture channel adjacent to the set screw.

In one aspect, the present invention relates to a knotless suture anchor device comprising: an anchor tip comprising an elongate cylindrical body having a proximal end and a distal end, an eyelet, a distal piercing tip, and at least two wing members extending laterally from the cylindrical body distal to the eyelet; and an anchor body comprising an elongate tubular body having a proximal end and a distal end, a screw thread positioned on an outer surface of the tubular body, and an inner lumen sized to fit the cylindrical body of the anchor tip.

In one embodiment, the anchor tip comprises a screw thread extending from the distal end of the cylindrical body towards the eyelet. In one embodiment, the anchor body comprises a screw thread positioned on an inner surface of the inner lumen mated to the screw thread of the anchor tip. In one embodiment, the at least two wing members each comprise a proximally facing surface and taper towards the piercing tip. In one embodiment, the piercing tip has a shape selected from the group consisting of: a conical tip, a pyramidal tip, a hypodermic needle tip, a wedge tip, a bladed tip, and a trocar tip.

In one embodiment, the anchor member is fabricated from a material selected from the group consisting of: PEEK, PAEK, PEKK, titanium, titanium-alloys, bioabsorbables, platinum, plastic, metal, and combinations thereof. In one embodiment, the eyelet is formed from a lumen passing through the cylindrical body from a first lateral opening to an opposing second lateral opening, such that the eyelet can accept at least one suture thread. In one embodiment, tubular body of the anchor body has a diameter that is larger than a diameter of the cylindrical body of the anchor tip and is smaller than a lateral extension of each of the at least two wing members.

In one embodiment, the anchor body is engageable to an outer driver of an anchor driver and the anchor tip is engageable to an inner driver of the anchor driver. In one embodiment, the outer driver rotates independently from the inner driver. In one embodiment, the inner driver comprises one or more tines that extend through the anchor body, past the anchor tip, and terminate in a penetrating tip complementing the piercing tip of the anchor tip. In one embodiment, the anchor driver is made from a metal and the anchor body and the anchor tip are each metal-free.

In one embodiment, the anchor tip has a length between about 5 mm to 20 about 50 mm and a diameter between about 5 mm to about 15 mm. In one embodiment, the anchor body has a length between about 5 mm to about 50 mm and a diameter between about 5 mm to about 20 mm.

In another aspect, the present invention relates to a method of attaching soft tissue to bone, the method comprising the steps of: providing the knotless suture anchor of claim 1 loaded onto an anchor driver; passing at least one suture thread through the eyelet of the anchor tip; driving the knotless suture anchor device into a bone of a subject, wherein the anchor tip forms a hole having a central diameter corresponding to a diameter of the anchor tip and lateral spaces adjacent to the central diameter corresponding to the at least two wing members; tensioning the at least one suture thread such that the at least one suture thread is positioned in the lateral spaces of the hole; and driving the anchor body over the anchor tip into the bone of the subject, such that the at least one suture thread is securely pinched only between a distal edge of the anchor body and the eyelet of the anchor tip, thereby locking the at least one suture thread in place.

In one embodiment, the knotless suture anchor is driven into a preformed hole in a bone of a subject. In one embodiment, the hole is formed using a tool selected from the group consisting of: an awl, a tap, and a drill. In one embodiment, the knotless suture anchor is punched or hammered directly into a bone of a subject without a preformed hole. In one embodiment, the at least one suture thread is re-tensioned by partially driving the anchor body out of the bone to free the at least one suture from the distal edge of the anchor body and the eyelet of the anchor tip. In one embodiment, a remainder of each of the at least one suture thread is positioned in the lateral spaces of the hole and is not engaged between the anchor body and the bone.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

FIG. 3A through FIG. 3C depict perspective views of an exemplary anchor device and an exemplary anchor driver of an exemplary knotless suture anchor system. FIG. 3A depicts a perspective view of an exemplary anchor device separated from an exemplary anchor driver. FIG. 3B depicts a perspective view of an exemplary anchor driver engaged with an exemplary anchor device. FIG. 3C depicts a perspective view of an exemplary anchor device.

FIG. 5A and FIG. 5B depict perspective views of internal components of an exemplary knotless suture anchor system. FIG. 5A depicts an exemplary set screw on an exemplary set screw driver, where both the exemplary set screw and exemplary set screw driver are internal to an exemplary suture fork. FIG. 5B depicts an exemplary set screw on an exemplary set screw driver.

FIG. 6A through FIG. 6C depict perspective views of an exemplary arrangement of an exemplary set screw driver, an exemplary suture fork, and an exemplary slider. FIG. 6A depicts a perspective view of an exemplary slider securing an exemplary set screw driver to an exemplary suture fork. FIG. 6B depicts a perspective view of an exemplary slider prior to being positioned in a securing position on an exemplary set screw driver and an exemplary suture fork. FIG. 6C depicts a perspective view of an exemplary slider securing an exemplary set screw driver to an exemplary suture fork.

FIG. 7A and FIG. 7B depict perspective views of operational states of an exemplary knotless suture anchor system. FIG. 7A is a perspective view of an exemplary knotless suture anchor system in an un-deployed configuration. FIG. 7B is a perspective view of an exemplary knotless suture anchor system in a deployed configuration.

FIG. 9A through FIG. 9J depict perspective and cutaway views depicting exemplary operational configurations of an exemplary knotless suture anchor system. FIG. 9A depicts perspective views of a first operational configuration (Top) and a second operational configuration (Bottom) of an exemplary torque wrench and an exemplary handle of an exemplary knotless suture anchor system. FIG. 9B depicts a cutaway view of a distal end of an exemplary knotless suture anchor system in an unengaged operation configuration. FIG. 9C depicts a cutaway view of a distal end of an exemplary knotless suture anchor system in an engaged operation configuration. FIG. 9D depicts a perspective view of suture anchor having a set screw driven in to fasten sutures within the suture anchor, leaving the sutures free from securement against bone, threading, and inner walls of the suture anchor. FIG. 9E depicts cutaway views of a distal end of an exemplary knotless suture anchor system comprising eyelet shuttles (left, center) and exemplary eyelet shuttles (right). FIG. 9F depicts a perspective (left) and cutaway (right) views of an exemplary knotless suture anchor with rigid ribs configured for push-in insertion. FIG. 9G depicts a perspective (left), cutaway (right), and a magnified view of a tab of an exemplary knotless suture anchor with flexing flaps configured for push-in insertion. FIG. 9H depicts a perspective (left) and side (right) view of an exemplary knotless suture anchor with rigid ribs and flexing tabs configured for push-in insertion with a range of exemplary rigid ribs and flexing tabs (bottom). FIG. 9I depicts perspective views of exemplary operational configurations of an exemplary knotless suture anchor system having a combined eyelet and threaded portion. FIG. 9J depicts side views of a combined eyelet and threaded portion with a "breakaway" style connection.

FIG. 10 depicts a side view of an exemplary knotless suture anchor device.

FIG. 12A and FIG. 12B depict cross-sectional views of an exemplary knotless suture anchor device. FIG. 12A depicts an exemplary knotless suture anchor device before deployment. FIG. 12B depicts an exemplary knotless suture anchor device in a deployed configuration.

FIG. 17A depicts a step of passing suture threads through an exemplary knotless suture anchor device. FIG. 17B depicts a step of punching an exemplary knotless suture anchor device into bone tissue, wherein the anchor tip is embedded in the bone tissue and the suture threads are freely tensionable. FIG. 17C depicts a step of screwing the anchor body over the anchor tip, wherein the suture threads are securely pinched between the distal end of the anchor body and the anchor tip. FIG. 17D depicts a step of removing the anchor driver from the knotless suture anchor device, wherein a top down view shows free ends of the suture threads positioned in lateral spaces adjacent to the knotless suture anchor device.

FIG. 22A through FIG. 22G depicts a series of images illustrating an exemplary method of repairing soft tissue to bone.

DETAILED DESCRIPTION

Figure 1:
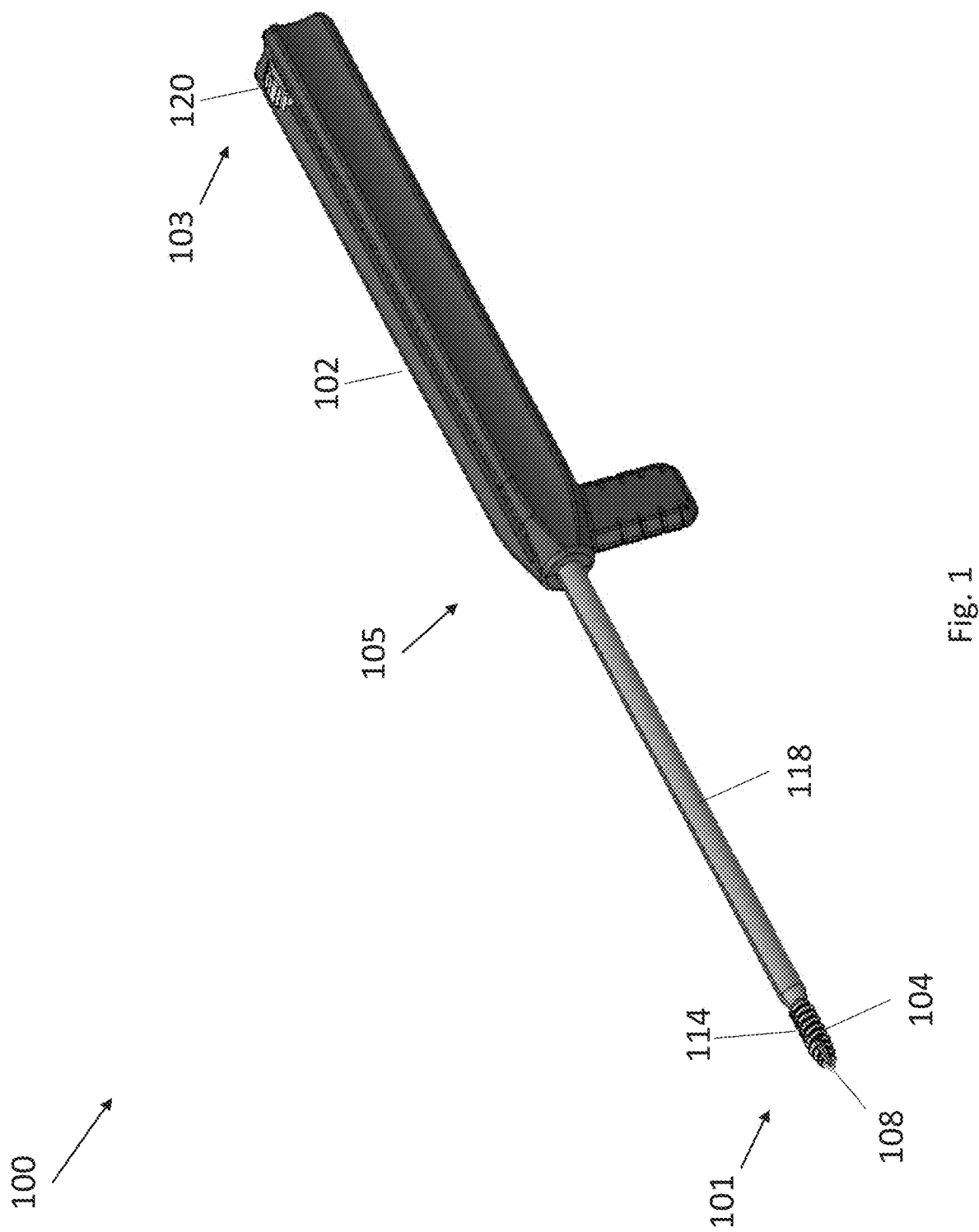
FIG. 1 depicts a perspective view of an exemplary knotless suture anchor system.

The present invention provides knotless suture anchor systems and devices for attaching soft tissue to bone. The systems and devices include suture anchors configured to engage and fasten sutures using set screws such that the locked sutures are free from frictional engagement with bone, screw threading, or internal walls of the anchors and set screws. Fastened sutures may also be re-tensioned by loosening a set screw to unfasten the sutures, adjusting the positioning of the sutures, and tightening the set screw to refasten the sutures. In some embodiments, the systems and devices enable the insertion of a suture anchor without preloading sutures, such that one or more sutures may be fastened to the suture anchor after implanting the suture anchor into a subject.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Knotless Suture Anchor System

Figure 2A:
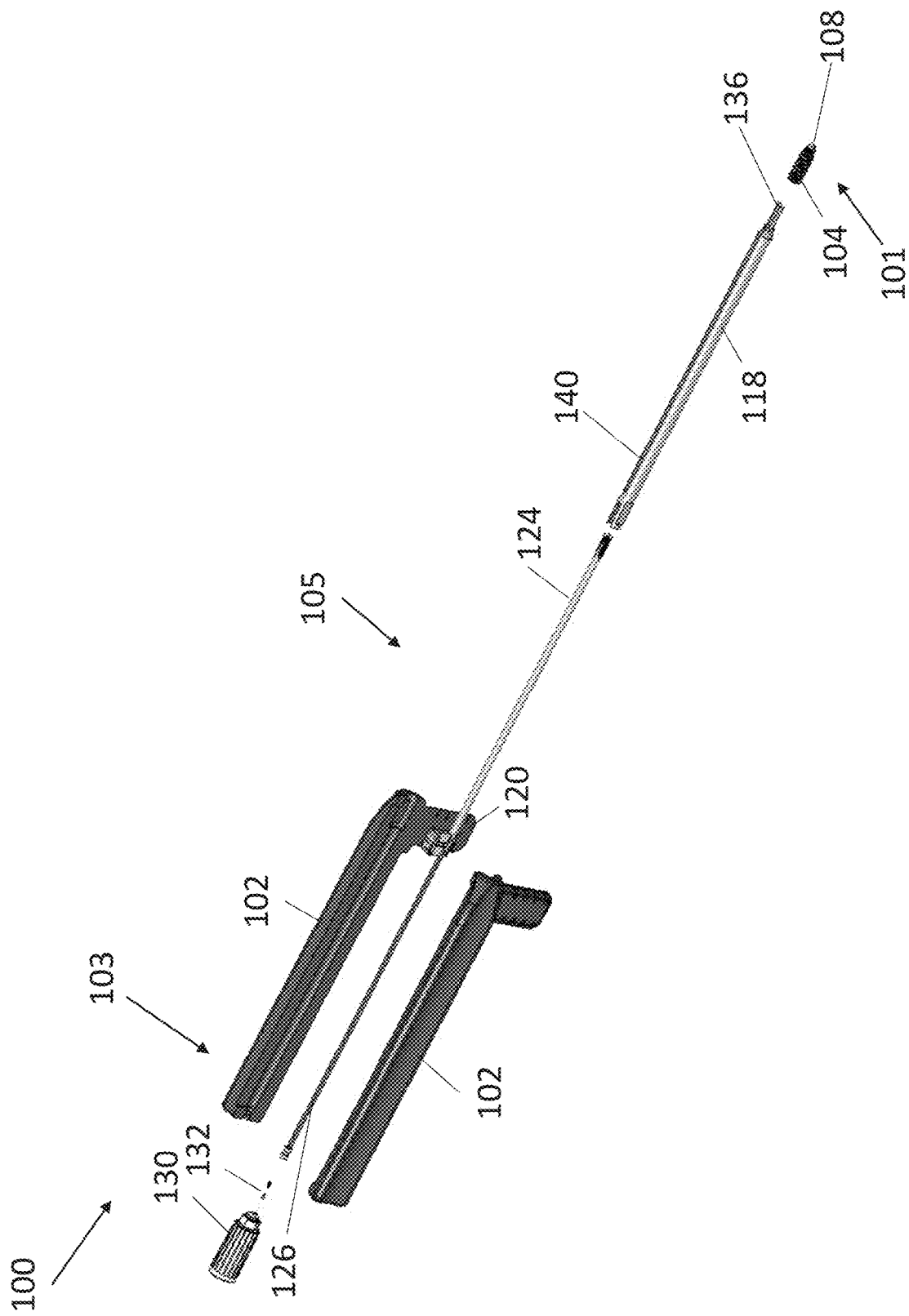
FIG. 2A depicts an exploded perspective view of an exemplary knotless suture anchor system.
Figure 2B:
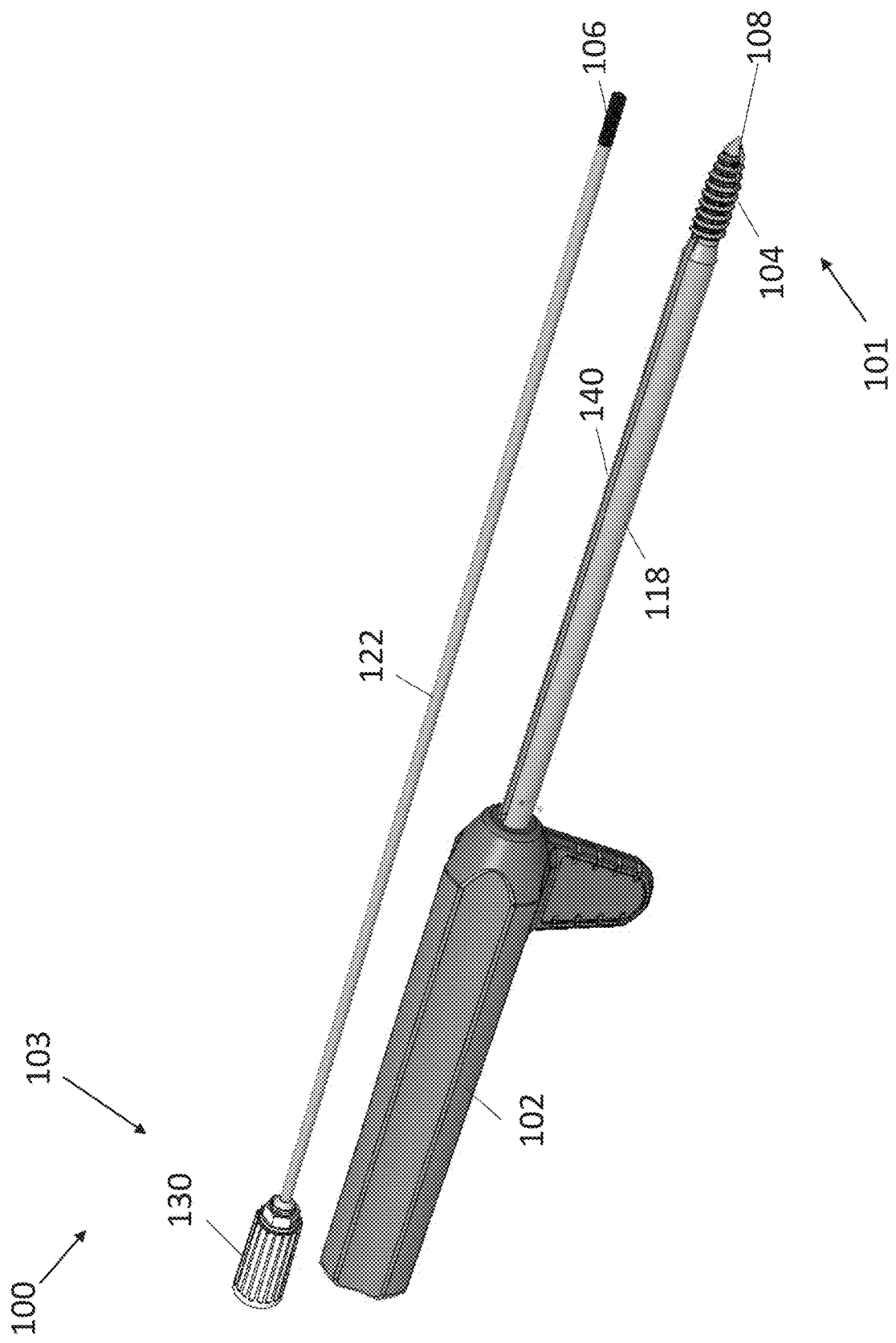
FIG. 2B depicts a perspective view of an exemplary knotless suture anchor system.
Figure 8:
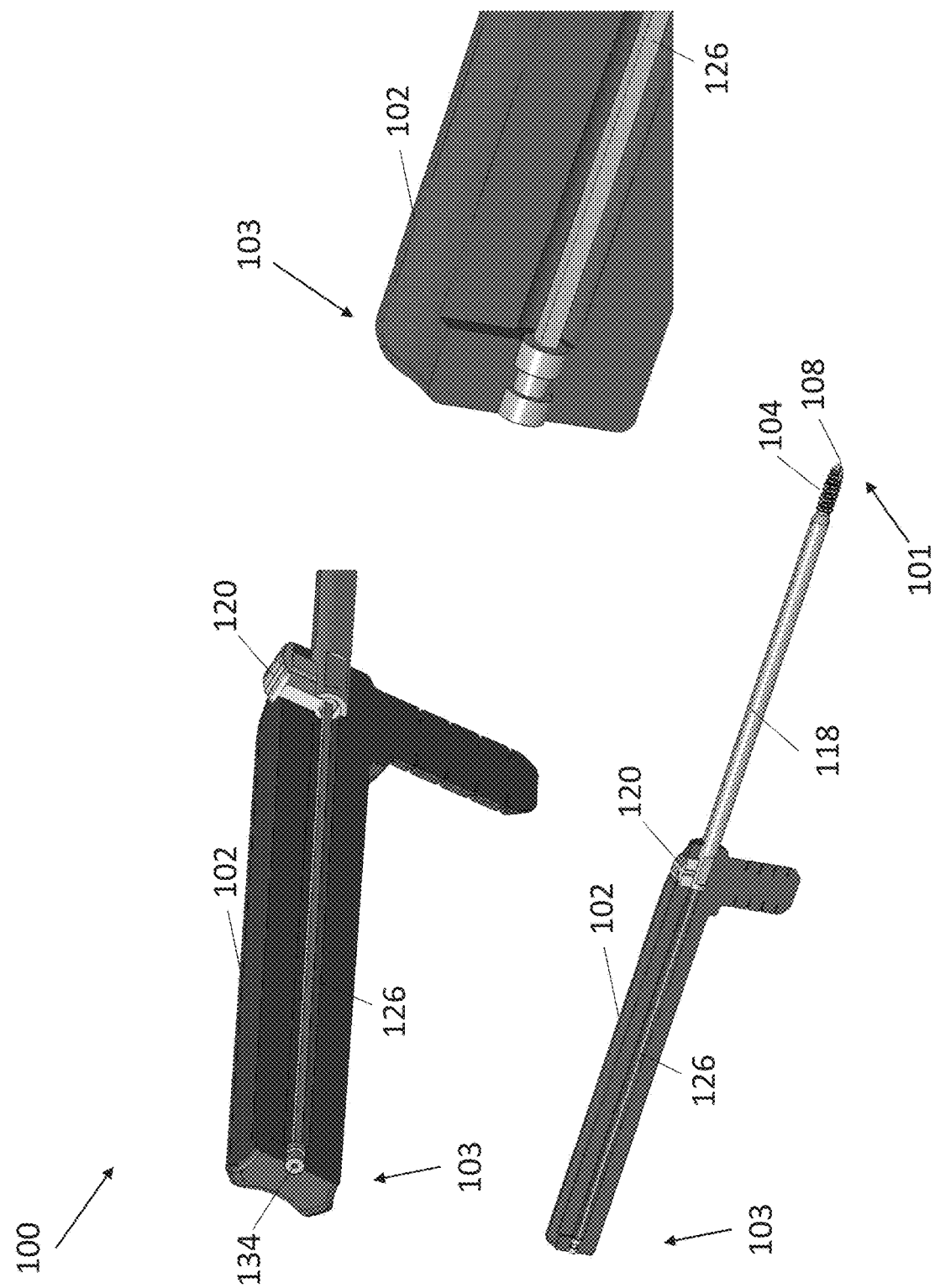
FIG. 8 depicts perspective views of an exemplary knotless suture anchor system in a deployed configuration.

Referring now to FIG. 1, FIG. 2A, and FIG. 2B, an exemplary knotless suture anchor system 100 is now described. System 100 comprises a suture anchor driver 105 having a distal end 101 and a proximal end 103, an anchor 104 engageable to the distal end of driver 105, and a set screw 106 loadable within driver 105 (visible in FIG. 5A and FIG. 5B). Driver 105 comprises a proximal handle 102, a distal shaft 118, and a continuous lumen extending from a proximal opening in handle 102 and a distal opening in shaft 118. The proximal opening of handle 102 is closed by a proximal end of drive shaft 126, which is an elongate rod that extends through the lumen of handle 102 and freely rotates about a longitudinal axis within handle 102 (FIG. 8). In some embodiments, the proximal end of drive shaft 126 can be slightly inset into the proximal end of handle 102, such that strikes from a mallet or hammer against the proximal end of handle 102 avoid hitting drive shaft 126. Driver 105 further comprises a set screw driver 122 positioned within its continuous lumen, wherein set screw driver 122 comprises an elongate tube shape with an internal lumen open at a proximal end and a set screw driving bit at a distal end engageable to a set screw 106 (visible in FIG. 5A and FIG. 5B).

A distal length of drive shaft 126 resides flush within a proximal lumen of set screw driver 122, wherein drive shaft 126 comprises a cross-sectional shape that is substantially the same as a cross-sectional shape of the lumen of set screw driver 122, such that rotating drive shaft 126 about a longitudinal axis also rotates set screw driver 122 about a longitudinal axis to drive its distal driving bit and an engaged set screw 106 into a suture anchor 104. Drive shaft 126 can be rotated using a torque wrench 130 having a torque wrench bit 132 that is compatible with a screw drive 134 of drive shaft 126. Set screw driver 122 is slidable from a proximal position in handle 102 to a distal position in shaft 118 by way of a slider 120 that is slidable through a slot in handle 102, wherein the positioning of set screw driver 122 can be controlled by sliding slider 120 along handle 102 (visible in FIG. 6A through FIG. 6C).

Figure 4A:
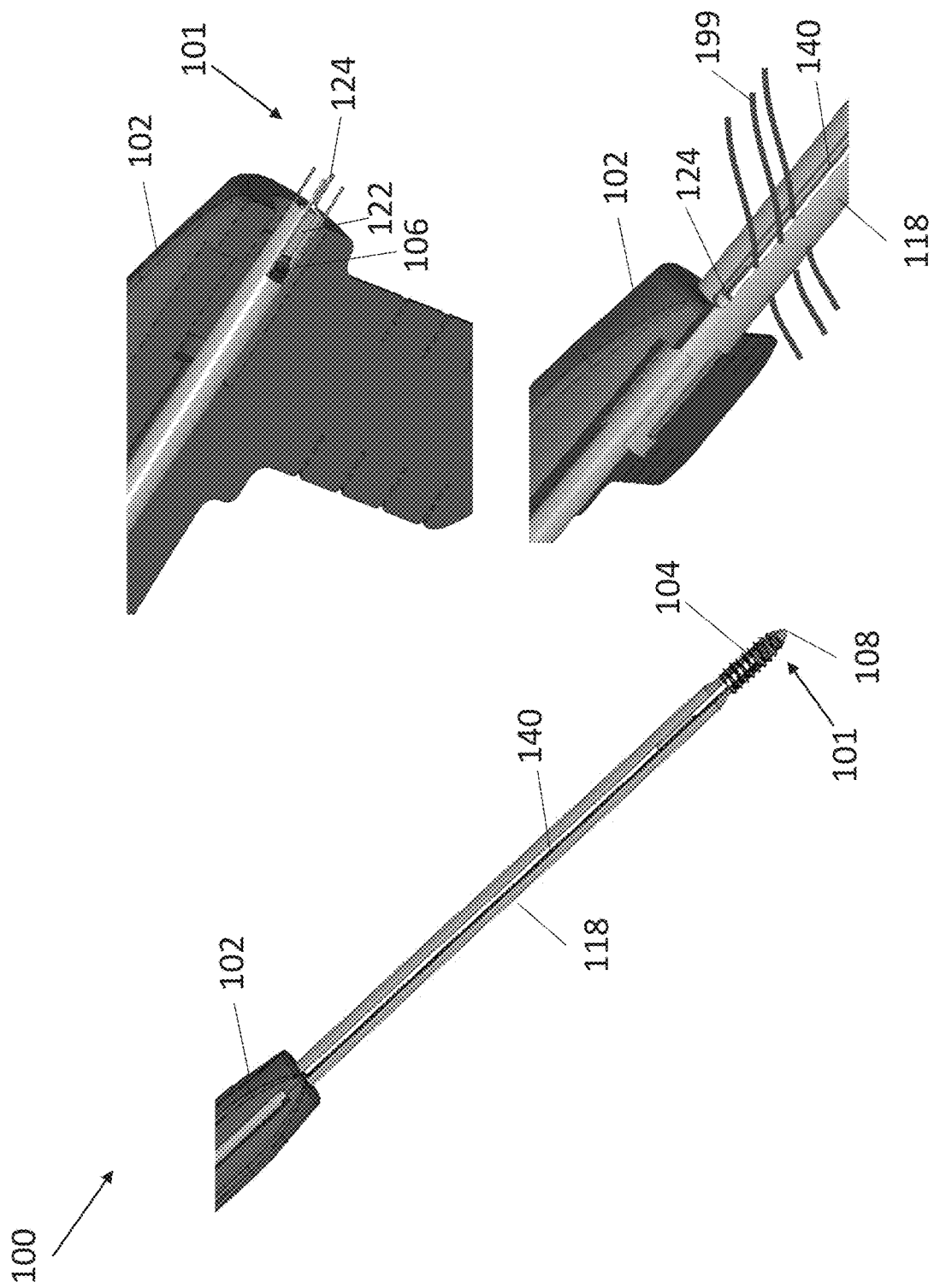
FIG. 4A depicts several views of an exemplary knotless suture anchor system. (Left) A perspective view of an exemplary anchor device and an exemplary anchor driver. (Top Right) A cutaway view of an exemplary suture fork, and an exemplary set screw driver in an exemplary handle. An exemplary anchor driver is hidden in this view. (Bottom Right) A cutaway view of an exemplary suture fork and an exemplary anchor driver in an exemplary handle.

Shaft 118 comprises an elongate tube-like shape having opposing longitudinal suture slots 140 that extend from a proximal section of shaft 118 through a distal tip of shaft 118 (visible in FIG. 4, left), wherein the distal tip of shaft 118 comprises suture anchor driver tip 136 configured to mate with anchor 104, as shown in FIG. 3A and FIG. 3B. One or more lengths of suture can be passed through the opposing longitudinal suture slots 140 for securement to a suture anchor 104 (visible in FIG. 7A). Sliding set screw driver 122 from a proximal position to a distal position pushes the one or more lengths of suture within the opposing longitudinal suture slots 140 into a suture anchor 104 for loading and securement with a set screw 106, as shown in FIG. 7B. In some embodiments, driver 105 can further comprise a suture shuttle 124 within its continuous lumen, wherein suture shuttle 124 sheathes over set screw driver 122 and an engaged set screw 106 (visible in FIG. 5A). Suture shuttle 124 comprises distal tines or forks configured to capture and center suture strands 199 such that suture strands 199 are aligned with the distal end of set screw driver 122.

Figure 2C:
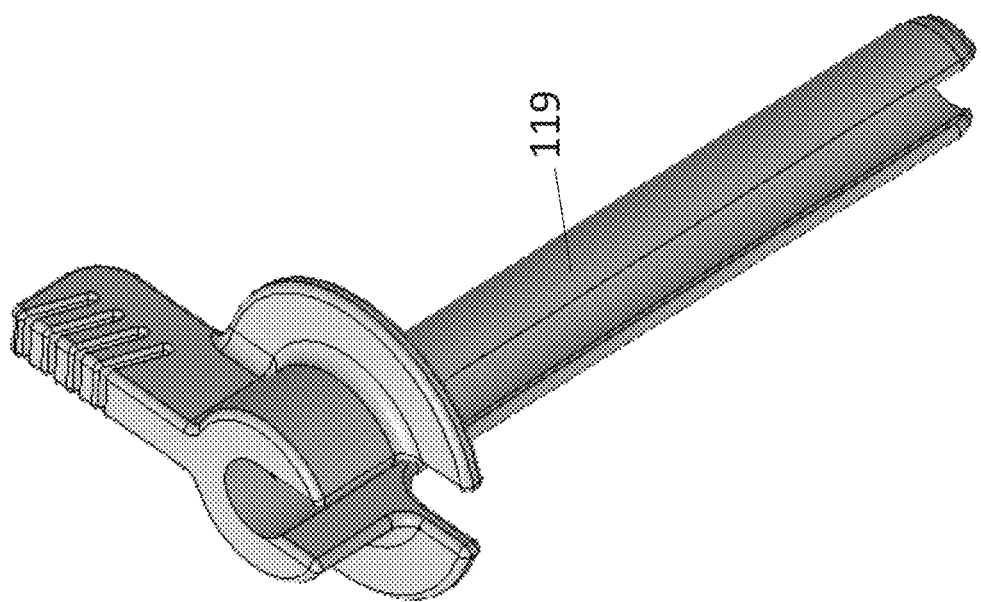
FIG. 2C depicts a perspective view of an exemplary suture blocking sleeve engageable to a shaft of a suture anchor driver.

Referring now to FIG. 2C, an exemplary suture blocking sleeve 119 is depicted. Suture blocking sleeve 119 comprises a substantially tube-like shape having a central lumen with an open lateral side. The central lumen is sized to engage shaft 118 of anchor driver 105 via a friction fit. In some embodiments, suture blocking sleeve 119 comprises a tab to facilitate securement and rotation about an engaged shaft 118. In a typical procedure, such as a minimally invasive arthroscopic surgery procedure, one or more cannulas are inserted into a subject for access to a surgical site and to guide instruments and hardware. A typical procedure may involve a step wherein one or more suture thread ends are routed through a cannula while the same cannula is used to insert and drive an anchor. Accordingly, a cannula is simultaneously occupied by one or more lengths of suture and a shaft 118 of anchor driver 105. As anchor driver 105 is rotated within the cannula to drive an anchor, the one or more lengths of suture may catch onto the driver (such as a longitudinal suture slot 140) and become twisted around shaft 118. To prevent twisting, suture blocking sleeve 119 may be fitted over shaft 118 prior to inserting anchor driver 105 into the cannula, such that the one or more lengths of suture threads are sandwiched between the cannula and suture blocking sleeve 119. Anchor driver 105 may then freely rotate to drive an anchor while an orientation and position of suture blocking sleeve 119 is maintained within the cannula to hold the one or more lengths of suture threads in place. After rotation of anchor driver 105 is completed, suture blocking sleeve 119 may be removed or rotated to align the open lateral side with a longitudinal suture slot 140 such that the one or more lengths of suture threads may be inserted into suture slot 140, captured by suture shuttle 124, and delivered to a distal end of anchor driver 105.

In various embodiments, driver 105 is amenable to any feature or modification to enhance or augment its function. For example, in some embodiments an exterior surface of handle 102 can comprise one or more textured surfaces or ridges configured to enhance a user's grip and to facilitate driving driver 105. In some embodiments, handle 102 can comprise one or more suture holders for temporary cinching or wrapping of suture threads and suture ends, such as the extension near the distal end of handle 102 in FIG. 1. In some embodiments, the proximal end of handle 102 can comprise a high-density polymer or a metal material configured to withstand repeated strikes from a hammer or mallet with minimal or no deformation. In some embodiments, such as in the exemplary embodiment shown in FIG. 2B for example, the set screw driver 122 is non-telescoping. In some embodiments, the torque wrench 130 comprises a uni-directional torque wrench which can be torque rated in a first rotational direction and fixed in a second rotational direction opposite the first rotational direction.

Referring now to FIG. 3A through FIG. 3C, an exemplary suture anchor 104 is now described. Suture anchor 104 comprises a substantially cylindrical shape having any suitable length and diameter. Suture anchor 104 can include one or more major threads 114 and one or more minor threads. In some embodiments, the minor threads are microthreads positioned between each thread 214, as described in U.S. Patent Publication No. 2018/0360438 (incorporated by reference herein in its entirety). While suture anchor 104 is depicted as having two minor threads positioned between each external thread 114, it should be understood that suture anchor 104 can comprise any number of threads having any desired pitch, angle, major diameter, and minor diameter. In some embodiments, suture anchor 104 comprises a tapered distal end terminating in a piercing tip 108. Piercing tip 108 is configured to pierce through and into tissue, including soft tissue and bone tissue. Piercing tip 108 can have any suitable shape, including but not limited to a conical tip, a pyramidal tip, a hypodermic needle tip, a wedge tip, a bladed tip, and the like. In some embodiments, piercing tip 108 is shaped from flat, angled facets. In some embodiments, piercing tip 108 is a trocar tip. In some embodiments, suture anchor 104 comprises one or more apertures 109, wherein apertures 109 connect an exterior of suture anchor 104 to an interior of suture anchor 104. Apertures 109 enable tissue ingrowth from an exterior of suture anchor 104 to enhance anchor pullout strength and biocompatibility.

Figure 9A:
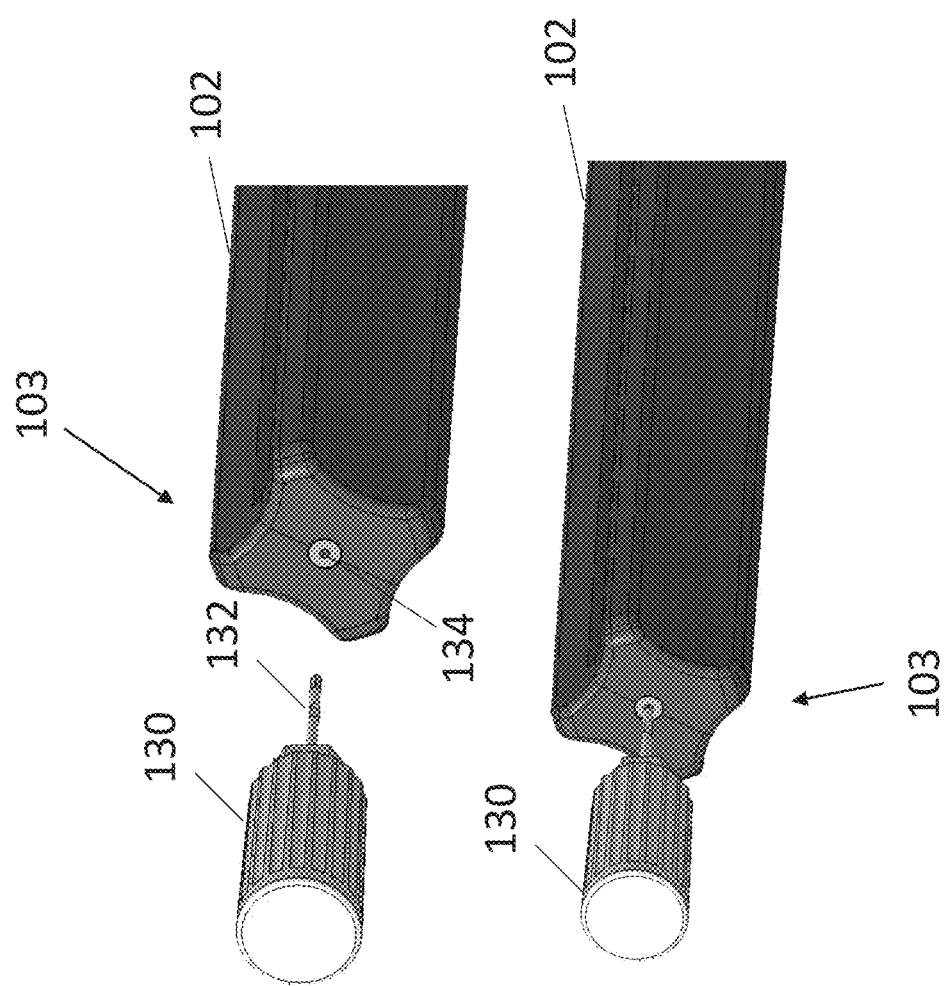

Suture anchor 104 can comprise one or more engagement structures compatible with suture anchor driver tip 136. For example, in the embodiment depicted in FIG. 3A through FIG. 3C, suture anchor 104 comprises anchor driver slots 138 having elongate channels sized to match the tines of suture anchor driver tip 136, wherein the engagement between suture anchor driver tip 136 and anchor driver slots 138 can be a friction fit. In some embodiments, engagement between suture anchor 104 and driver 105 can optionally further include a string or wire threaded through suture anchor 104 and pulled taut against driver 105. For example, openings visible in FIG. 3C indicate the entry and exit locations of a retention thread channel 142 that loops through the body of suture anchor 104. In some embodiments, retention thread channel 142 loops underneath suture channel 116 such as to avoid crossing through suture channel 116, as shown in FIG. 9B and FIG. 9C. The string or wire can be provided to maintain an engagement between suture anchor 104 and driver 105 prior to insertion into a subject and can be removed before insertion into a subject or after insertion into a subject.

Suture channel 116 extends from a proximal opening in suture anchor 104 and has an oblong cross-sectional shape and opposing thread regions 112, wherein suture channel 116 terminates within suture anchor 104 at a distal suture channel face 117. While suture channel 116 is depicted as being visible from lateral sides of suture anchor 104 to promote ingrowth of tissue in a subject, it should be understood that suture channel 116 may also be fully or partially enclosed on lateral sides of suture anchor 104. The opposing thread regions 112 extend for a height of suture channel 116 and are mated to set screw thread 110 of set screw 106 (depicted in FIG. 5B and demonstrated in FIG. 9B and FIG. 9C). Since set screw 106 comprises a circular cross-sectional shape, the oblong cross-sectional shape of suture channel 116 reserves lateral spaces adjacent to a set screw 106 that has been driven into suture channel 116. The lateral spaces thereby form channels through which lengths of suture 199 may reside without frictional engagement with suture anchor 104 or set screw 106. Accordingly, any lengths of suture 199 that are fastened between suture anchor 104 and set screw 106 are securely pinched and tensioned between the distal end of set screw 106 and distal suture channel face 117 as shown in FIG. 9C.

In some embodiments, system 100 can further comprise an eyelet shuttle 148 configured to shuttle a suture 199 into anchor 104, wherein eyelet shuttle 148 forms a high friction path in which to engage a suture 199. Referring now to FIG. 9E, exemplary eyelet shuttles 148 are depicted. Eyelet shuttle 148 comprises a substantially cylindrical body extending between a proximal tab 150 and a distal end 152, wherein the body comprises an eyelet 154 configured to receive a suture 199 therethrough. In some embodiments, eyelet shuttle 148 further comprises an interference rib extending from a proximal end of eyelet 154 in a distal direction. Anchor 104 accordingly comprises a shuttle slot 144 configured to receive a complementary eyelet shuttle 148, wherein shuttle slot 144 is embedded in suture channel face 117 and extends towards a distal end of anchor 104. In some embodiments, shuttle slot 144 further comprises a proximal tab slot 146 embedded in suture channel face 117, wherein tab slot 146 is configured to receive a complementary proximal tab 150. Complementary components are configured to seat within an opening or slot with sufficient clearance to fit sutures 199 in an engageable and releasable manner, such as in a friction fit.

The body of eyelet shuttle 148 comprises a diameter that is narrower than an inner diameter of shuttle slot 144 such that shuttle slot 144 is configured to receive both eyelet shuttle 148 and a suture threaded thereon. Proximal tab 150 extends laterally from the diameter of the body of eyelet shuttle 148 such that proximal tab 150 is wider than the inner diameter of shuttle slot 144. While proximal tab 150 is depicted in FIG. 9E as forming two opposing tabs, it should be understood that proximal tab 150 can have any form, including but not limited to three, four, five, six, or more tabs equally or irregularly spaced about the body of eyelet shuttle 148, as well as a cap form similar to a screw head that is circular, ovular, square, rectangular, hexagonal, and the like. Proximal tab 150 is configured to abut against distal suture channel face 117 such that a suture 199 is engageable between proximal tab 150 and distal suture channel face 117 (FIG. 9E, left). In some embodiments wherein anchor 104 comprises a proximal tab slot 146 (FIG. 9E, center), proximal tab 150 is configured to abut against a distal face of proximal tab slot 146 such that a suture 199 is engageable between proximal tab 150 and the distal face and inner lateral sides of proximal tab slot 146. In some embodiments, the body of eyelet shuttle 148 comprises a distal end 152 having a diameter that is wider than the diameter of the body of eyelet shuttle 148, such that distal end 152 is flush or near flush with the inner diameter of shuttle slot 144 and is configured to stabilize insertion of eyelet shuttle 148 into shuttle slot 144.

Figure 9F:
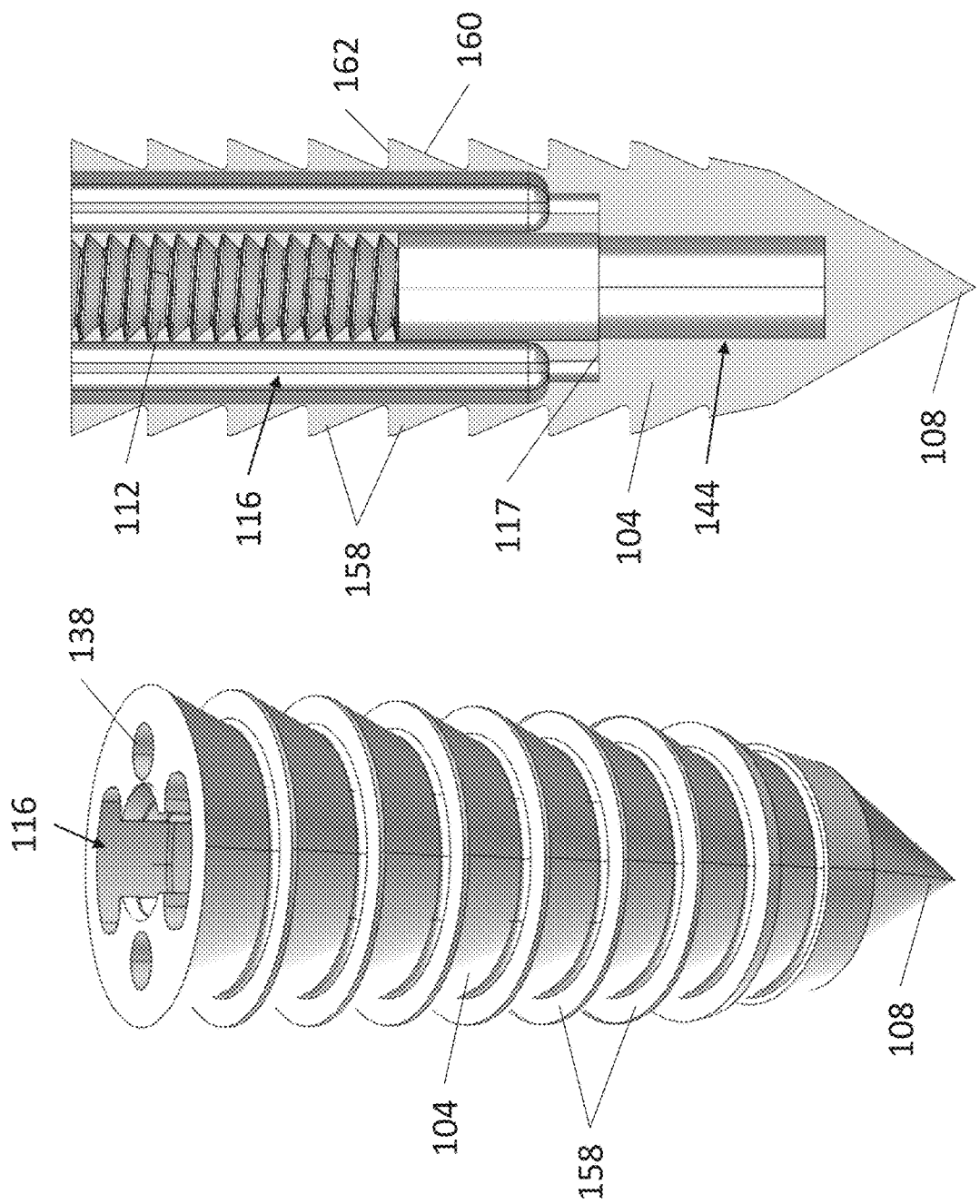
Figure 9G:
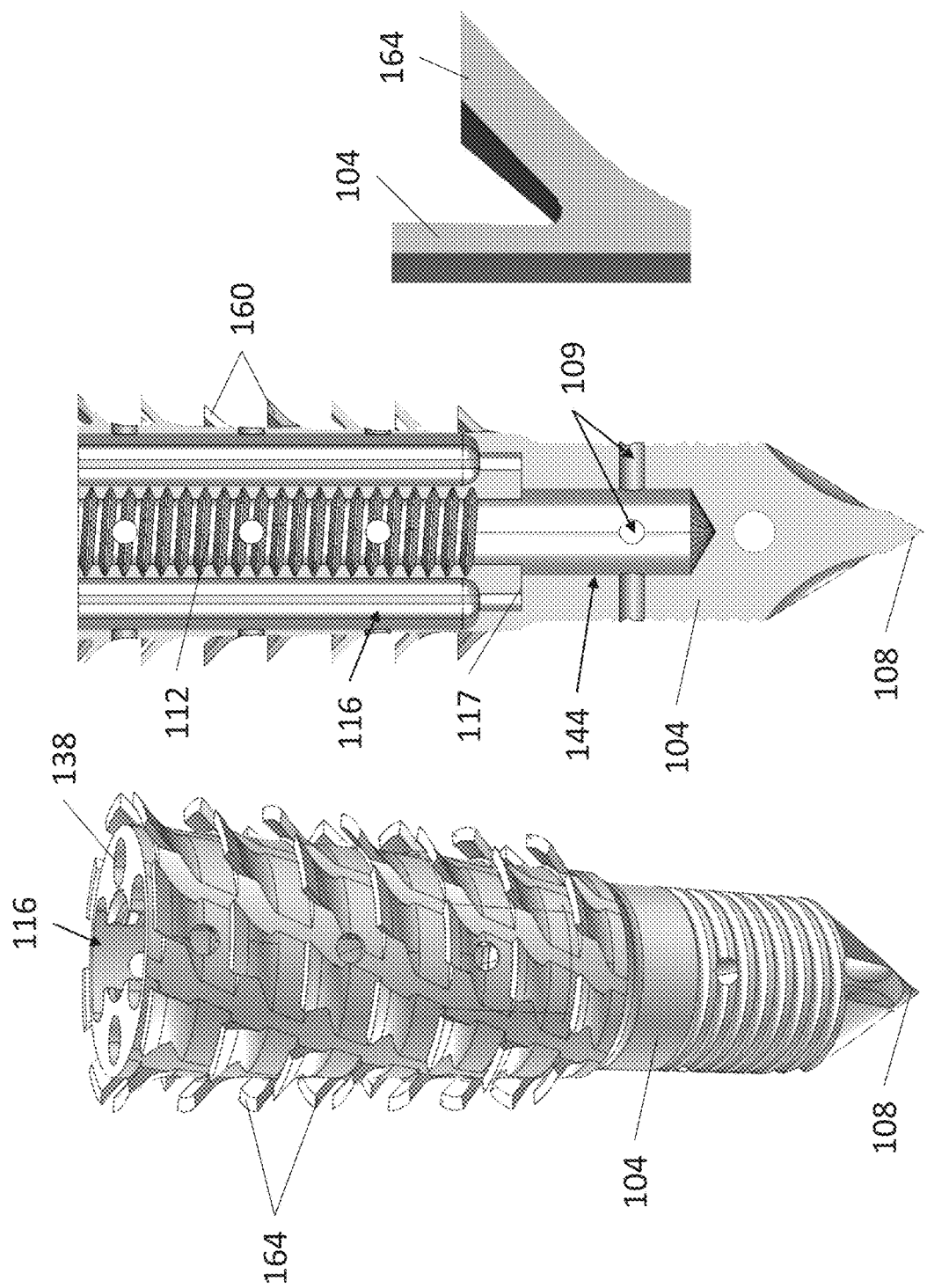
Figure 9H:
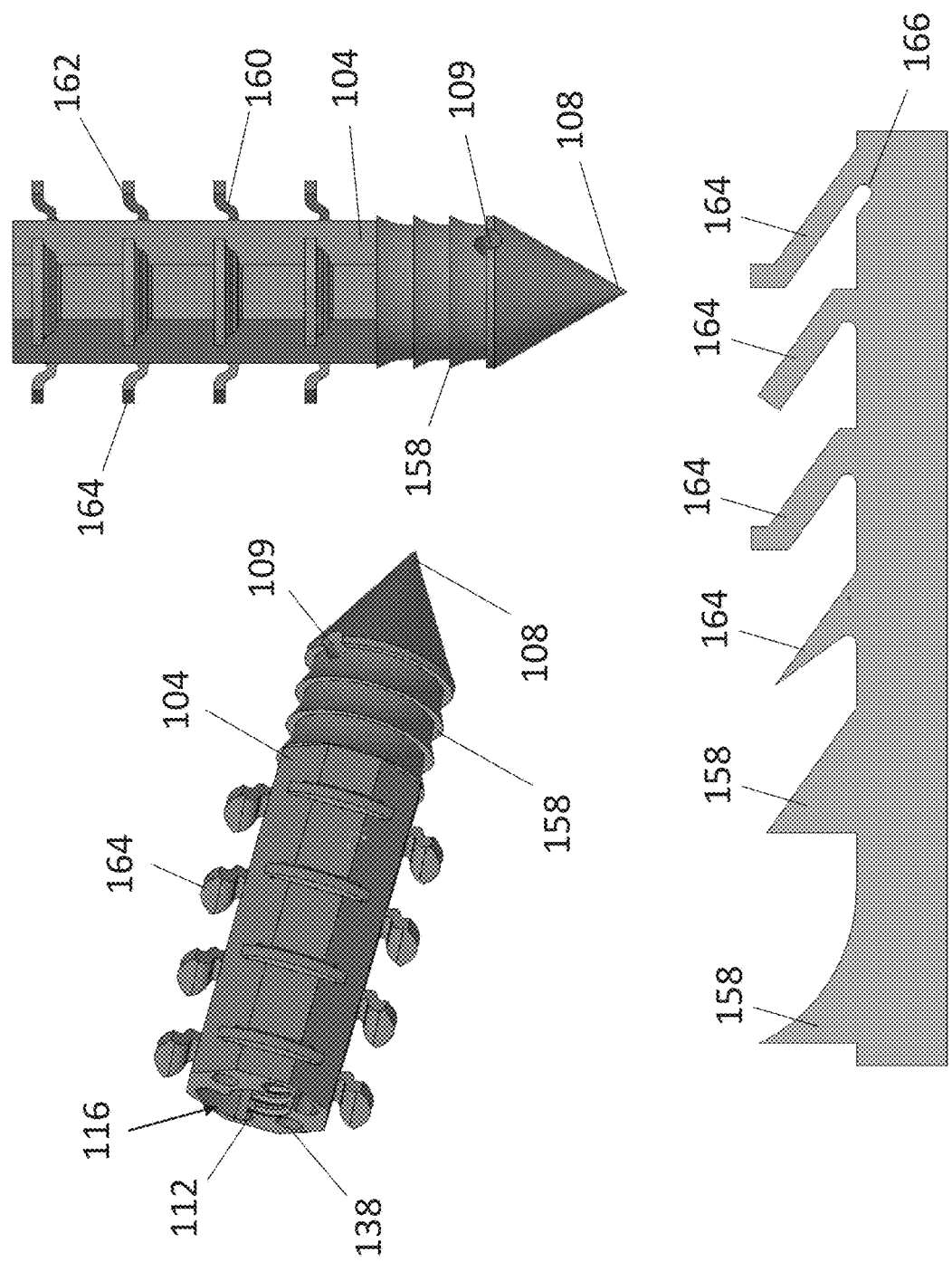

In some embodiments, the knotless suture anchor devices are configured for push-in insertion. Push-in insertion refers to an insertion method that is not entirely reliant on a screwing-in motion. Anchors can be push-in inserted by hammering or back-and-forth twisting motions, either into a pre-existing hole or directly into native tissue. Anchor devices configured for push-in insertion can have threaded exteriors as well as unthreaded exteriors. Referring now to FIG. 9F, FIG. 9G and FIG. 9H, exemplary knotless suture anchors 104 configured for push-in insertion are depicted. FIG. 9F relates to an anchor 104 comprising exterior rigid ribs 158, FIG. 9G relates to an anchor 104 comprising exterior flexing flaps 164, and FIG. 9H relates to an anchor 104 comprising an alternative embodiment comprising rigid ribs 158 and exterior flexing flaps 164. Similar to anchors 104 described elsewhere herein, anchors 104 configured for push-in insertion comprise internal structures sized and configured to receive set screws and suture threads, such that suture threads are releasably securable to an anchor 104 with the ability to re-tension suture threads by adjusting the set screws. Accordingly, each of the anchors 104 depicted in FIG. 9F through FIG. 9H comprises internal anchor threads 112 configured to mate to a set screw 106, suture channels 116 adjacent to internal anchor threads 112 configured to route suture threads, and suture channel faces 117 configured to engage suture threads against an inserted set screw 106. In some embodiments, anchors 104 configured for push-in insertion comprise a shuttle slot 144 for compatibility with eyelet shuttles 148, as described elsewhere herein. In various embodiments, anchors 104 configured for push-in insertion comprise a distal piercing tip 108, apertures 109, and proximal anchor driver slots 138 as described elsewhere herein.

Referring now to FIG. 9F, anchor 104 having rigid ribs 158 is now described in detail. Each rigid rib 158 encircles an exterior of anchor 104 to form a ring-like shape. Rigid ribs 158 cover at least a portion of an exterior of anchor 104. In some embodiments, rigid ribs 158 cover an entire length of anchor 104. Rigid ribs 158 each comprise a distal angled face 160 that facilitates insertion in a distal direction towards piercing tip 108 and a proximal face 162 angled to resist being pulled out. In some embodiments, proximal face 162 is substantially flat and aligned substantially orthogonal to a longitudinal axis of anchor 104. In some embodiments, proximal face 162 is angled such that an edge of each rigid rib 158 formed between distal face 160 and proximal face 162 points in a proximal direction. In various embodiments, rigid ribs 158 are machined from the same material as anchor 104.

Referring now to FIG. 9G, anchor 104 having flexing flaps 164 is now described in detail. Flexing flaps 164 extend out of anchor 104 in a proximal direction away from piercing tip 108. Flexing flaps 164 can have any desired dimensions. For example, flexing flaps 164 can each have a thickness between about 0.1 mm and 1 mm, or about 0.3 mm, and can each extend for a length between about 0.2 mm and 2 mm, or about 1.75 mm. Flexing flaps 164 cover at least a portion of an exterior of anchor 104. In some embodiments, flexing flaps 164 cover an entire length of anchor 104. While flexing flaps 164 are depicted as forming a substantially spiral-like pattern on anchor 104, it should be understood that flexing flaps 164 can be formed in any desired pattern. Flexing flaps 164 are configured to be compressible against anchor 104 to facilitate insertion in a distal direction. As flexing flaps 164 extend in a proximal direction, pulling against an inserted anchor 104 induces each flexing flap 164 to dig into adjacent tissue and naturally flare outwards from piercing tip 108, thereby resisting being pulled out. In various embodiments, flexing flaps 164 are machined from the same material as anchor 104.

Referring now to FIG. 9H, anchor 104 having rigid ribs 158 and flexing flaps 164 is now described in detail. Rigid ribs 158 extend out of anchor 104 in a proximal direction away from piercing tip 108 along a length of the body of anchor 104. Flexing flaps 164 extend out of anchor 104 in a proximal direction away from piercing tip 108 along a length of the body 104. Rigid ribs 158 and flexing flaps 164 can have any desired dimensions. For example, rigid ribs 158 or flexing flaps 164 can each have a thickness between about 0.1 mm and 1 mm, or about 0.3 mm, and can each extend for a length between about 0.2 mm and 2 mm, or about 1.75 mm. Rigid ribs 158 and/or flexing flaps 164 cover at least a portion of an exterior of anchor 104. Rigid ribs 158 and flexing flaps 164 can be formed in any desired pattern. Flexing flaps 164 are configured to be compressible against anchor 104 to facilitate insertion in a distal direction. As flexing flaps 164 extend in a proximal direction, pulling against an inserted anchor 104 induces each flexing flap 164 to dig into adjacent tissue and naturally flare outwards from piercing tip 108, thereby resisting being pulled out. In some embodiments, flexing flaps 164 may recede into the body of anchor 104 to aid in insertion to bone. In some embodiments, a flexing flap recess 166 allows flexing flaps 164 to recede into the body of anchor 104 to reduce stress on anchor 104 and the proximal end of flexing flap 164. In various embodiments, rigid ribs 157 and flexing flaps 164 are machined from the same material as anchor 104. Also shown in FIG. 9H (bottom) are exemplary rigid ribs 158 and flexing flaps 164 that may extend out of anchor 104, including an embodiment of flexing flap recess 166

In some embodiments, a push-in insertion anchor 104 comprises one or more flexible ribs or spines (not pictured). The flexible ribs have a retracted position and an extended position. In a retracted position, the flexible ribs are flush with an exterior surface of anchor 104 or withdrawn within anchor 104, such that the flexible ribs do not impede insertion in a distal direction. Furthermore, in a retracted position, the flexible ribs may comprise an inner tab or node that impedes into the space of internal anchor thread 112. After insertion, an anchor 104 may receive one or more suture threads followed by a set screw 106 to secure the one or more suture threads, as described elsewhere herein. As the set screw 106 is driven into the space of internal anchor thread 112, the inner tab or node of the flexible ribs are pushed out to shift the flexible ribs into an extended position. In an extended position, the flexible ribs dig into adjacent tissue to enhance anchor pullout strength. In some embodiments, the flexible ribs extend outwards in a lateral direction. In some embodiments, the flexible ribs extend outwards in a lateral and proximal direction.

Suture anchors 104 can have any desired dimensions. In various embodiments, anchors 104 can have a length between about 5 mm to about 50 mm and a diameter between about 3 mm to about 30 mm. For example, anchor 104 may be 2.4 mm in diameter and 10 mm in length.

Anchors 104 can be described as having an outer diameter or major diameter and an inner diameter or minor diameter, wherein the outer or major diameter refers to a diameter of anchors 104 including exterior structures (such as threading, ribs, or flaps), and the inner or minor diameter refers to a diameter of anchors 104 excluding exterior structures. In some embodiments, the size of the exterior structures can be characterized in terms of a difference between the outer/major diameter and the inner/minor diameter. For example, in various embodiments, the outer/major diameter and the inner/minor diameter can differ by between about 0.2 mm to 2 mm, such that the exterior structures extend out from anchor 104 by a distance between about 0.1 mm to 1 mm.

Figure 9I:
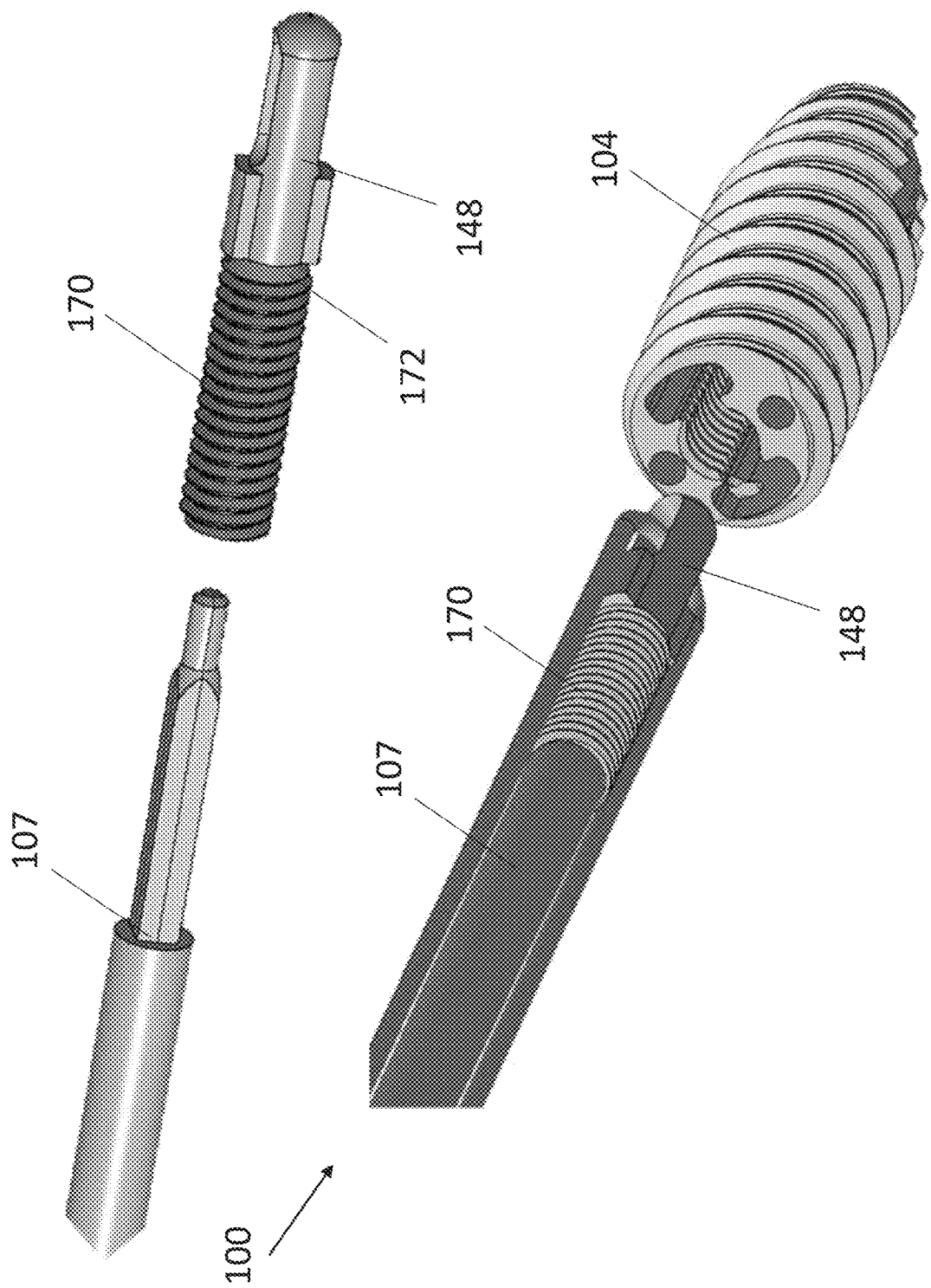
Figure 9J:
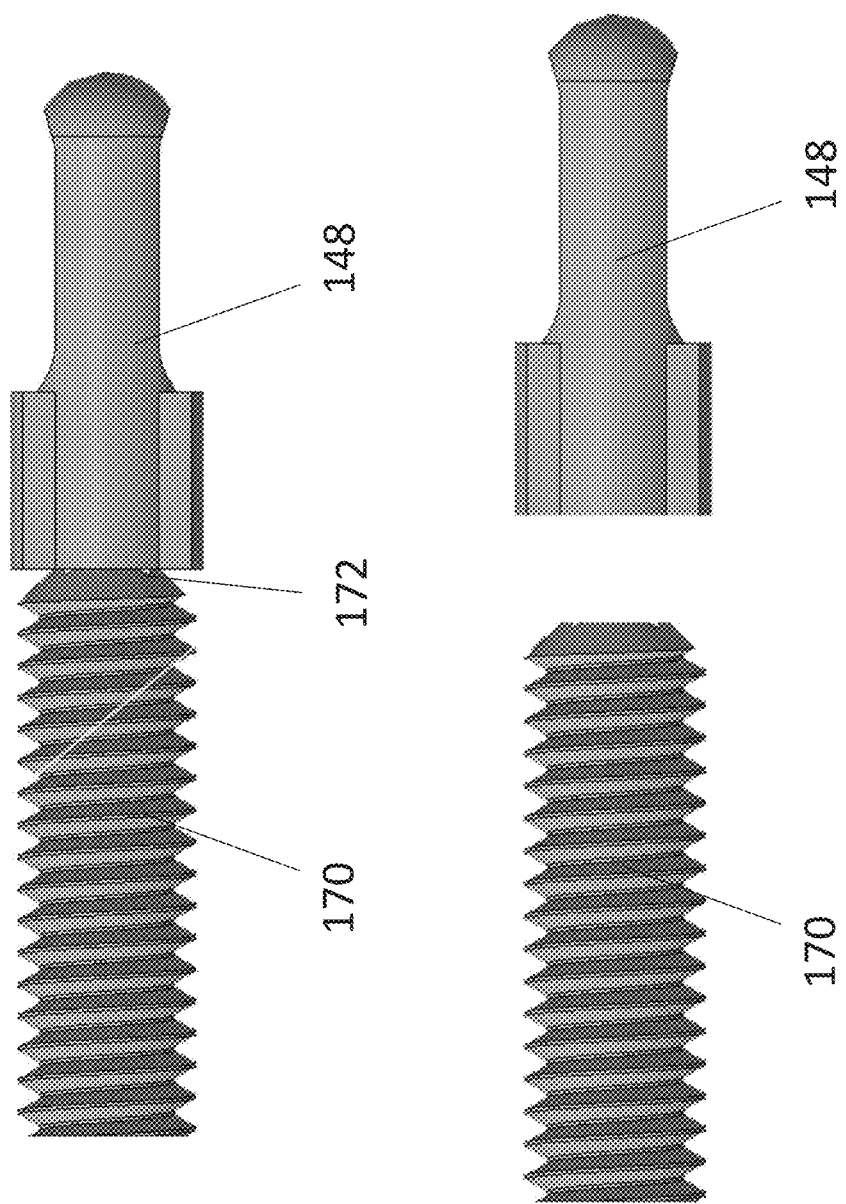

Referring now to FIG. 9I, an exemplary knotless suture anchor device 100 wherein the body of eyelet shuttle 148 has a threaded portion 170 formed as a single piece connected by a thin bridge of plastic 172 to be inserted into anchor 104. In one embodiment, thin bridge of plastic 172 breaks when eyelet shuttle 148 is held stationary in anchor 104. In one embodiment, thin bridge of plastic 172 breaks when a driver rotating threaded portion 172 and eyelet shuttle 148 exceeds a specified torque value. In one embodiment, threaded portion 170 helps to position and orient eyelet shuttle 148 before inserting into anchor 104. Displayed in FIG. 9J is the eyelet shuttle 148 joined to the threaded portion 170 by thin bridge of plastic 172 (top). Also shown is eyelet shuttle 148 broken away from threaded portion 170 (bottom).

Figure 11:
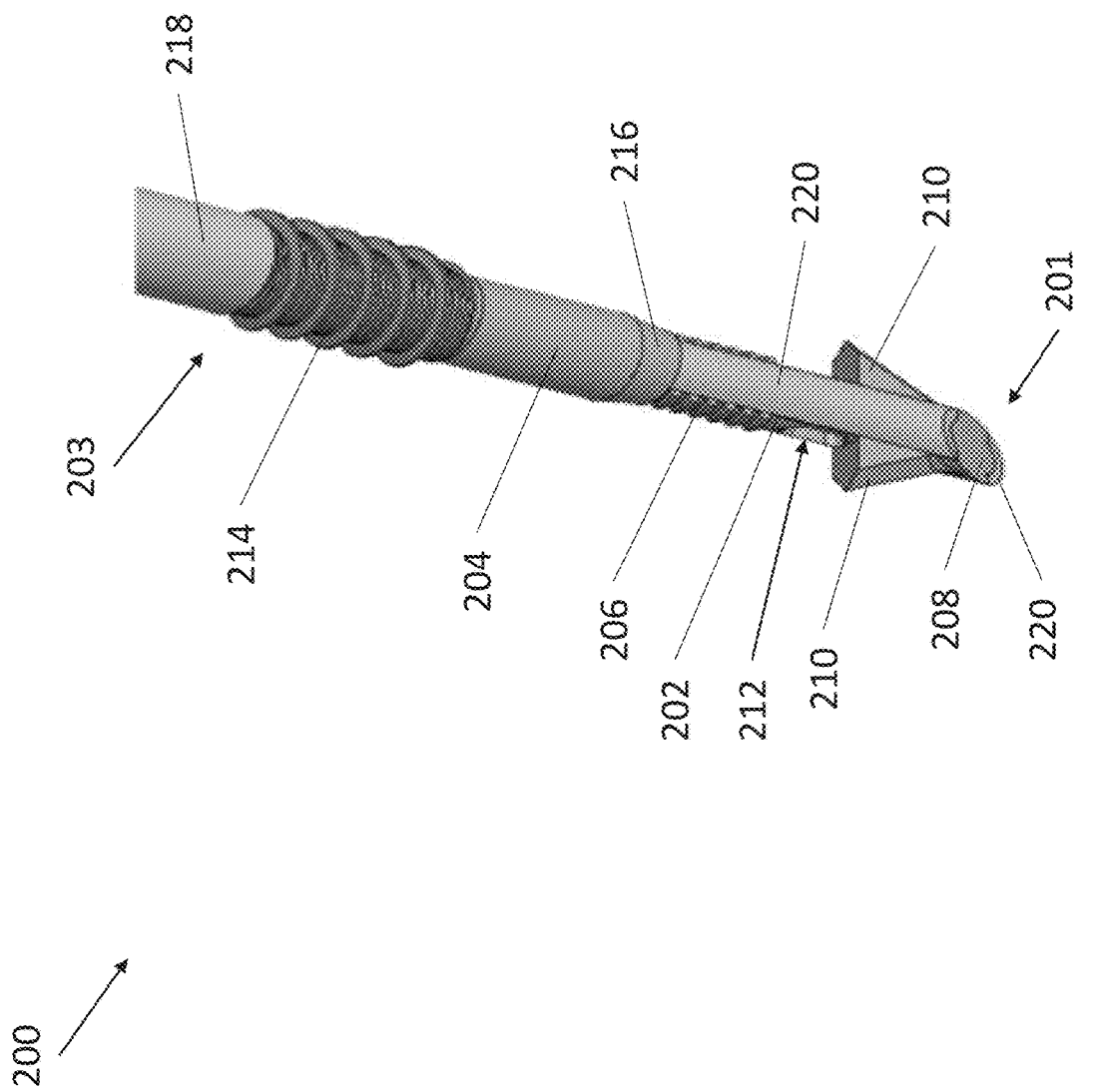
FIG. 11 depicts a perspective view of an exemplary knotless suture anchor device.

Referring now to FIG. 10 and FIG. 11, an exemplary knotless suture anchor device 200 is depicted loaded onto a suture anchor driver 218. Device 200 comprises an anchor tip 202 positioned at a distal end 201 and an anchor body 204 positioned at a proximal end 203. Anchor tip 202 has an elongate cylindrical body having a distal piercing tip 208 and an eyelet 212 positioned proximal to piercing tip 208. In some embodiments, anchor tip 202 comprises a thread 206 fully or partially extending from distal end 203 of the cylindrical body to eyelet 212.

Visible in FIG. 11, anchor tip 202 further comprises at least two wing members 210 extending laterally from the elongate body, wherein wing members 210 are positioned distal to eyelet 212. In some embodiments, wing members 210 comprise a proximally facing surface and taper towards piercing tip 208. Wing members 210 can have any suitable cross-sectional shape, including but not limited to circular, rectangular, square, and the like. Wing members 210 prevent rotational movement in anchor tip 202 and can have any suitable orientation on anchor tip 202. For example, wing members 210 depicted in FIG. 11 are linearly oriented but can also be angled at any desired degree relative to each other. Additional wing members 210 can form further orientations such as a "Y" orientation or an "X" orientation. In some embodiments, the proximally facing surfaces of wing members 210 are orthogonal to a long axis of the elongate body. In other embodiments, the proximally facing surfaces of wing members 210 may be angled in a proximal direction, such as to form a "V" shape. Such angling may help prevent anchor pullout from tissue.

Piercing tip 208 is configured to pierce through and into tissue, including soft tissue and bone tissue. Piercing tip 208 can have any suitable shape, including but not limited to a conical tip, a pyramidal tip, a hypodermic needle tip, a wedge tip, a bladed tip, and the like. In some embodiments, piercing tip 208 is shaped from flat, angled facets. In some embodiments, piercing tip 208 is a trocar tip.

Eyelet 212 is configured to receive suture threads and is formed by a lumen passing through the cylindrical body of anchor tip 202 from a first lateral opening to an opposing second lateral opening. Eyelet 212 can have any suitable cross-sectional shape, including circular, elliptical, rectangular, and the like. In some embodiments, eyelet 212 is sized to freely pass a plurality of suture threads as well as any knots formed in the suture threads.

Anchor tip 202 can have any suitable length, shape, and diameter. For example, anchor tip 202 can have a length between about 5 mm to about 50 mm and a diameter between about 3 mm to about 30 mm.

Anchor body 204 has an elongate tubular body with a proximal screw thread 214. Proximal screw thread 214 can include one or more major threads and one or more minor threads. In some embodiments, the minor threads are microthreads positioned between each thread 214, as described in U.S. Patent Publication No. 2018/0360438 (incorporated by reference herein in its entirety). In some embodiments, anchor body 204 comprises a distal tapered end 216. Anchor body 204 further comprises a hollow inner lumen sized to fit over the cylindrical body of anchor tip 202. In some embodiments, anchor body 204 comprises a screw thread on an inner surface of the lumen mated to thread 206 of anchor tip 202, such that anchor body 204 is configured to screw onto anchor tip 202. In other embodiments, the inner lumen of anchor body 204 is threadless, such that anchor body 204 can freely slide over anchor tip 202. In some embodiments, anchor body 204 further comprises a locking cam that is engageable with anchor tip 202, such that the locking cam locks anchor body 204 to anchor tip 202 and prevents movement between anchor body 204 and anchor tip 202.

Anchor body 204 can have any suitable length, shape, and diameter, wherein the diameter of anchor body 204 is larger than the diameter of the cylindrical body of anchor tip 202. For example, anchor body 204 can have a length between about 5 10 mm to about 50 mm and a diameter between about 3 mm to about 30 mm.

Suture anchor driver 218 comprises an outer driver and an inner driver. The inner driver is mated to anchor tip 202 and is configured to drive anchor tip 202. The outer driver actuates independently from the inner driver and has a distal bit end mated to proximal end 203 of anchor body 204, wherein the distal bit end of the outer driver is configured to drive anchor body 204. In various embodiments, any driver having a compatible distal bit end can be used to drive anchor body 204. In some embodiments, the locking cam of the anchor body 204 is unlocked when the distal bit end of the outer driver is engaged to the anchor body 204 and the locking cam is locked when the distal bit end of the outer driver is disengaged from the anchor body 204. In some embodiments, the inner driver comprises one or more tines 220, wherein the one or more tines 220 extend through anchor body 204 and past anchor tip 202 to terminate in a penetrating tip complementing piercing tip 208. The penetrating tip combining the one or more tines 220 and piercing tip 208 enhances penetration of device 200 through soft tissue and into bone. In some embodiments, tines 220 are positioned external to anchor tip 202 (as depicted in FIG. 10 and FIG. 11). In some embodiments, tines 220 are positioned internal to and extend through anchor tip 202 (as depicted in FIG. 12A and FIG. 12B).

Figure 13:
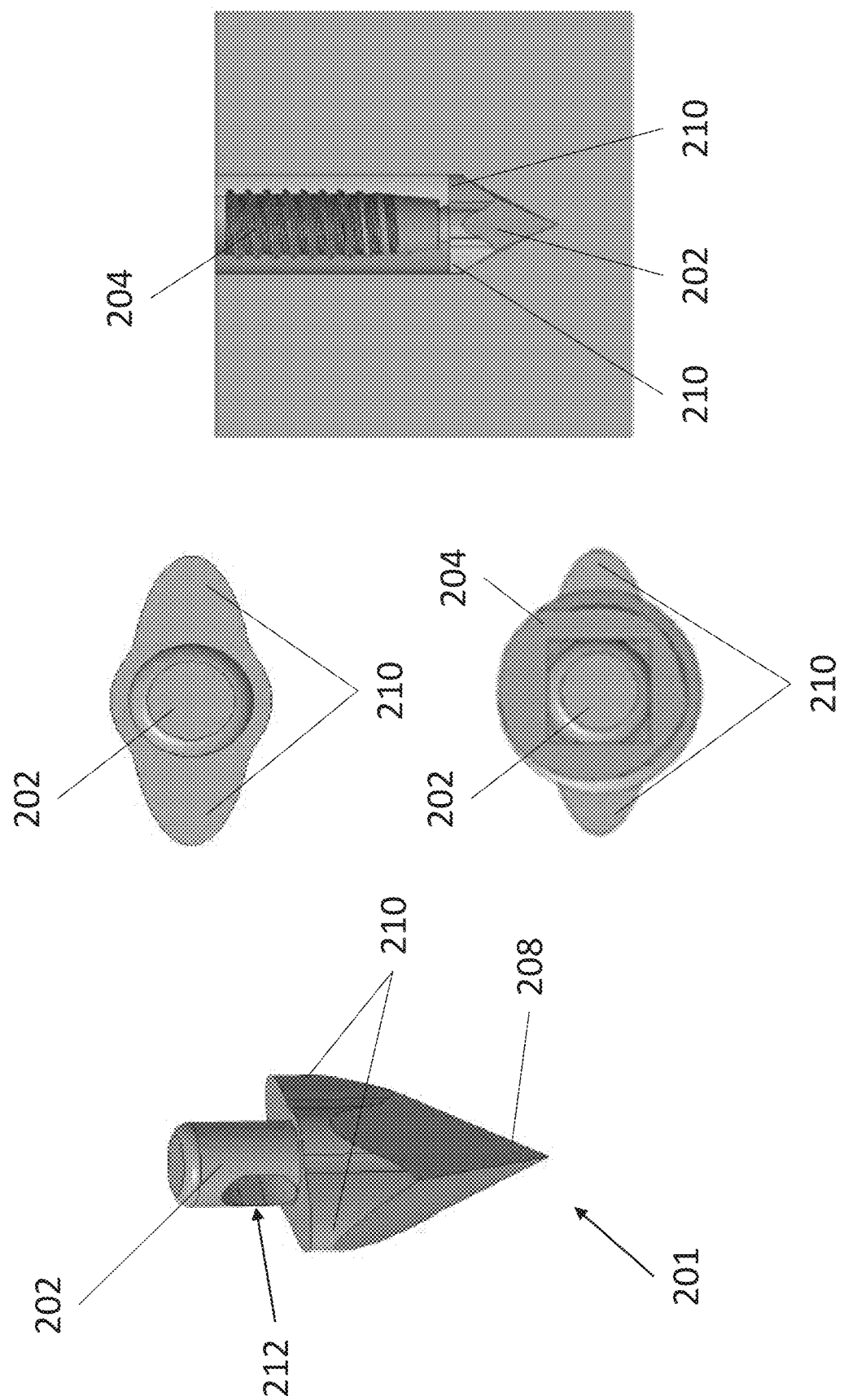
FIG. 13 depicts several views of an exemplary knotless suture anchor tip with and without an anchor body attached. (Left) A perspective view of an anchor tip. (Top middle) A top down view of an anchor tip. (Bottom middle) A top down view of an anchor tip with an anchor body attached. (Right) a side view of an anchor tip with an anchor body attached embedded in bone tissue.

Referring now to FIG. 13, several schematic views of anchor tip 202 and anchor body 204 are depicted. As described elsewhere herein, anchor tip 202 comprises at least two laterally protruding wing members 210 that increase the cross-sectional area of anchor tip 202 (FIG. 13, left, top middle). Upon penetration into tissue, anchor tip 202 forms a hole having a diameter corresponding to the diameter of the cylindrical body of anchor tip 202, wherein the hole further comprises lateral spaces adjacent to the hole diameter corresponding to wing members 210. Anchor body 204 and external thread 214 have a combined diameter greater than the diameter of the cylindrical body of anchor tip 202, such external thread 214 is configured to dig into and engage surrounding tissue as anchor body 204 is screwed onto anchor tip 202. It should be noted that the diameter of anchor body 204 does not exceed the lateral protruding wing members 210 (FIG. 13, bottom middle). The lateral spaces in the hole formed by anchor body 202 thereby remain unobstructed by anchor body 204 (FIG. 13, right).

As described above, anchor tip 202 is configured to receive and freely pass at least one suture thread through eyelet 212. Sutures present in eyelet 212 are secured by screwing anchor body 204 onto proximal end 203 of anchor tip 202. As anchor body 204 advances over anchor tip 202 in a distal direction, a distal edge of anchor body 204 passes over and closes eyelet 212 until each of the at least one suture thread in eyelet 212 is securely pinched and tensioned between the distal edge of anchor body 204 and eyelet 212. The at least one suture thread can be freed from the grip between the distal edge of anchor body 204 and eyelet 212 by advancing anchor body 204 in a proximal direction, permitting re-tensioning of the sutures. In some embodiments, the at least suture thread can be securely pinched and tensioned between the distal edge of anchor body 204 and proximally facing surfaces of wing members 210.

The knotless suture anchor devices and associated anchor drivers of the present invention can be made from any suitable material, including but not limited to metals, non-biodegradable polymers, biodegradable polymers, polymer composites, copolymers, and bioceramics. The term biodegradable as used herein is defined to mean materials that degrade in the body and then are either absorbed into or excreted from the body. The term bioceramic as defined herein is defined to mean ceramic and glass materials that are compatible with body tissue and can be biodegradable or non-biodegradable. Contemplated metals include stainless steel, titanium, alloys of nickel and titanium, or other biocompatible metallic materials. The separable components of the various suture anchors described herein may be fabricated from the same material or different materials. For example, in some embodiments anchor tip 202 and anchor body 204 are metal-free and anchor driver 218 comprises metal tines 220. As described elsewhere herein, metal tines 220 complement piercing tip 208 of anchor tip 202 to enhance tissue penetration.

Non-biodegradable polymers include but are not limited to polyethylene, polypropylene, PEEK (polyetheretherketone), PAEK (Polyaryletherketone), or other biocompatible non-absorbable polymers. Biodegradable polymers include but are not limited to aliphatic polyesters, polyorthoesters, polyanhydrides, polycarbonates, polyurethanes, polyamides and polyalkylene oxides. In some embodiments, the biodegradable polymers are aliphatic polyester polymers and copolymers, and blends thereof. The aliphatic polyesters are typically synthesized in a ring opening polymerization. Suitable monomers include but are not limited to lactic acid, lactide (including L-, D-, meso and D,L mixtures), glycolic acid, glycolide, epsilon, caprolactone, p-dioxanone (1,4-dioxan-2-one), trimethylene carbonate (1,3-dioxan-2-one), delta-valerolactone, and combinations thereof.

Bioceramics include but are not limited to ceramics comprising mono-, di-, tri-, alpha-tri-, beta-tri-, and tetra-calcium phosphate, hydroxyapatite, calcium sulfates, calcium oxides, calcium carbonates, magnesium calcium phosphates. In addition to bioceramics, bioglasses may also be used. The bioglasses may include phosphate glasses and bioglasses.

Additional contemplated polymers can include poly (amino acids), copoly(ether-esters), polyalkylene oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, polyurethanes, poly(ether urethanes), poly(ester urethanes), polypropylene fumarate), poly(hydroxyalkanoate), homopolymers and copolymers of lactide (which includes lactic acid, D-,L- and meso lactide); glycolide (including glycolic acid); .epsilon.-caprolactone; p-dioxanone (1,4-dioxan-2-one); trimethylene carbonate (1,3-dioxan-2-one); alkyl derivatives of trimethylene carbonate; .delta.-valerolactone; .beta.-butyrolactone; .gamma.-butyrolactone; .epsilon.-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; .alpha.,.alpha. diethylpropiolactone; ethylene carbonate; ethylene oxalate; 3-methyl-1, 4-dioxane-2,5-dione; 3,3-diethyl-1,4-dioxan-2,5-dione-; 6,6-dimethyl-dioxepan-2-one; 6,8-dioxabicycloctane-7-one and polymer blends thereof. Additional exemplary polymer or polymer blends include, by non-limiting example, a polydioxanone, a polyhydroxybutyrate-co-hydrox-yvalerate, polyorthocarbonate, a polyaminocarbonate, and a polytrimethylene carbonate.

In one aspect, the present invention relates to a driver for facilitating the insertion of the anchor into bone. In some embodiments, the driver is comprised of a superelastic, pseudoelastic and/or "shape memory" material, such as nitinol, to allow the driver to advance the anchor along a curved path. In some embodiments, the driver has a proximal feature that can be twisted to advance a threaded anchor into the bone.

Figure 19A:
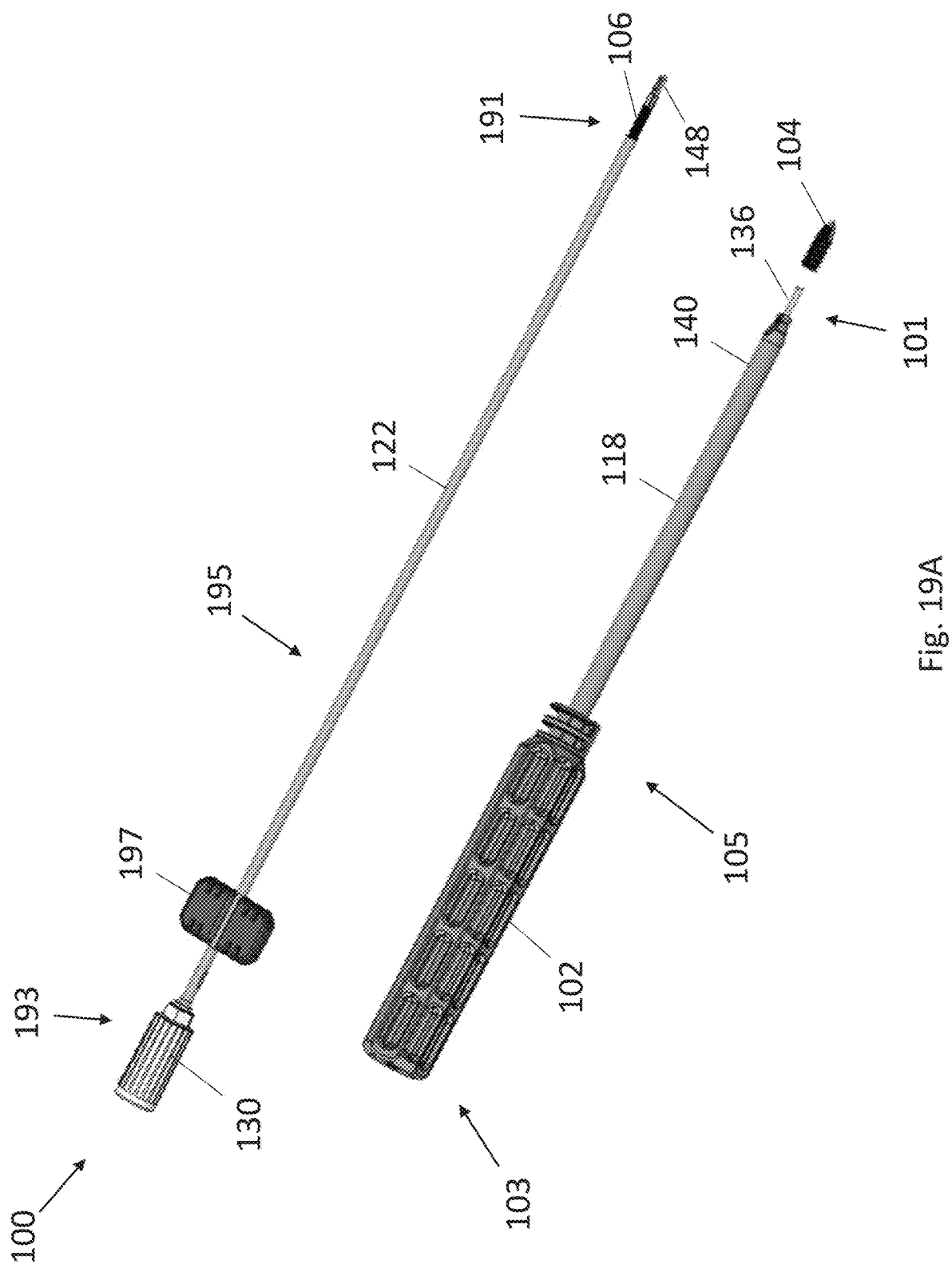
FIG. 19A depicts a perspective view of an exemplary knotless suture anchor system.

Now referring now to FIG. 19A, an exemplary knotless suture anchor system 100 is now described. System 100 comprises a suture anchor driver 105 having a distal end 101 and a proximal end 103, an anchor 104 engageable to the distal end of driver 105. System 100 further comprises a shuttle driver 195 having a distal end 191, a proximal end 193, with set screw 106 and eyelet shuttle 148 loadable on the distal end of shuttle driver 195. Anchor driver 105 comprises a proximal handle 102, a distal shaft 118, and a suture anchor driver tip 136 configured to mate with anchor 104. Shuttle driver 195 comprises a proximal torque wrench 130, set screw driver 122, wherein set screw driver 122 comprises an elongate tube shape and a set screw driving bit at the distal end engageable to a set screw 106 and eyelet shuttle 148. Rotating anchor driver 105 about a longitudinal axis also rotates distal shaft 118, suture anchor driver tip 136 and an engaged suture anchor 104 to be inserted into bone. Rotating torque wrench 130 of shuttle driver 195 about a longitudinal axis also rotates screw driver 122 and an attached set screw 106 to insert eyelet shuttle 148 into a locked position in anchor 104.

Figure 19B:
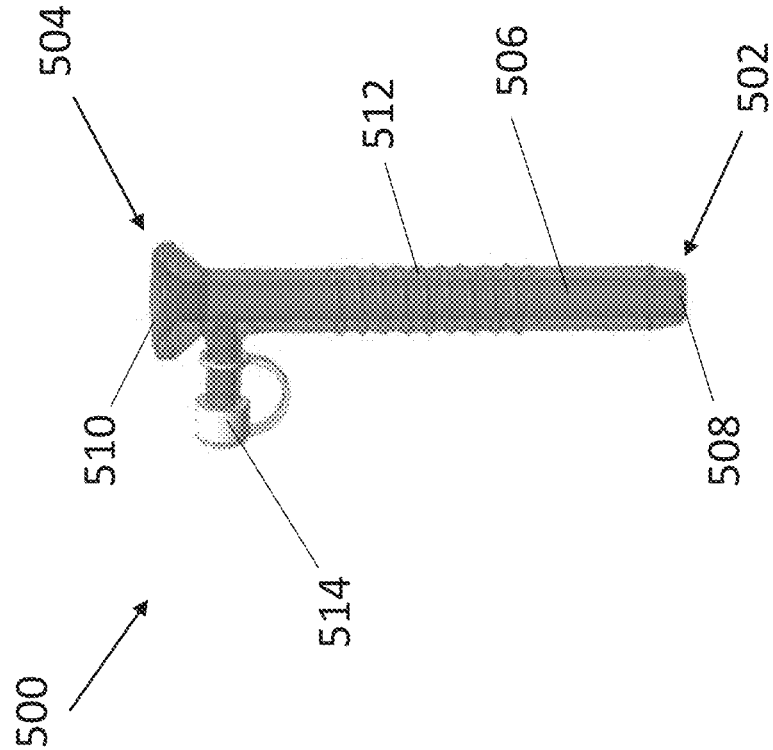
FIG. 19B depicts a side view of an exemplary drill guide according to an aspect of the present invention.

In one aspect, the present invention relates to a drill guide for facilitating the insertion of an anchor using a driver. Now referring to FIG. 19B, a drill guide 500 comprising a distal end 502 and a proximal end 504, and a cannula 506 extending from distal opening 508 and proximal opening 510. Drill guide 500 has grip 512 comprising ridges that extend a length along the body of drill guide 500 from the proximal to distal end. In some embodiments, distal end 502 of drill guide 500 is inserted subcutaneously to provide access to a drilling and/or anchoring site in the bone. In some embodiments, the distal end 502 of drill guide 500 comprises docking tines to support fixation in the bone. In some embodiments, the proximal end 504 of drill guide 500 comprises a surface such that strikes from a mallet or hammer against the proximal end will fix the drill guide into the bone. In some embodiments, drill guide 500 has one or more proximal openings 510 on proximal end 504 to accept an anchor inserter, driver, drill, suture retrieval component, and/or obturator. In some embodiments, drill guide 500 comprises one or more lumens within cannula 506 wherein an anchor, suture, anchor inserter, driver, drill, suture retrieval component, and/or obturator may pass through to the site on the bone. In some embodiments, the drill guide has two lumens wherein one is for drilling and the other is for anchor introduction. In some embodiments, drill guide 500 has a tapered tip at distal end 502 that allows the drill and anchor to converge to the same insertion path. In some embodiments, the drill guide has buttons 514 that lock the drill and anchor into various positions, including, but not limited to, full retraction away from the bone, or full advancement into the bone. In some embodiments, the drill guide may be loaded with a non-coring obturator to improve and ease advancement through soft-tissue and can be used percutaneously. In some embodiments, the drill guide has an angled tip at distal end 502, for example 20°, to facilitate the placement of the drill and anchor on an angled surface. In some embodiments, the drill can remain in the drill guide while the anchor is being inserted.

Figure 20A:
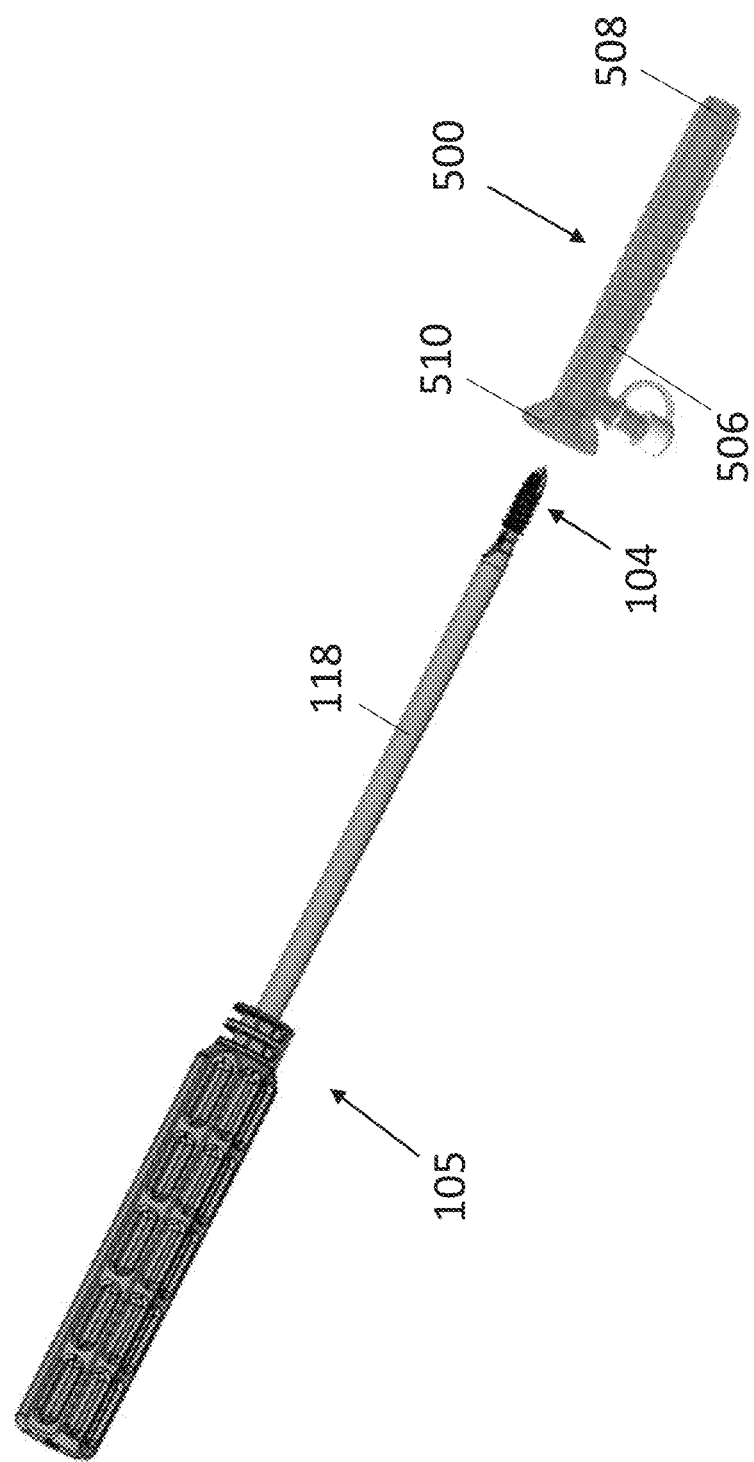
FIG. 20A and FIG. 20B depicts a perspective view of an exemplary knotless suture anchor system with a drill guide according to an aspect of the present invention.

Now referring to FIG. 20A, anchor driver 105 with an attached anchor 104 is inserted into proximal opening 510 of drill guide 500. Distal shaft 118 and anchor 104 proceed through cannula 506 of drill guide 500 to exit out of distal opening 508 and reach the bone. In some embodiments, the suture anchor is driven into a preformed hole in the bone, which may be formed using a tool such as an awl, tap, drill, or the like. In some embodiments, the suture anchor is punched or hammered directly into bone without a preformed hole.

Figure 20B:
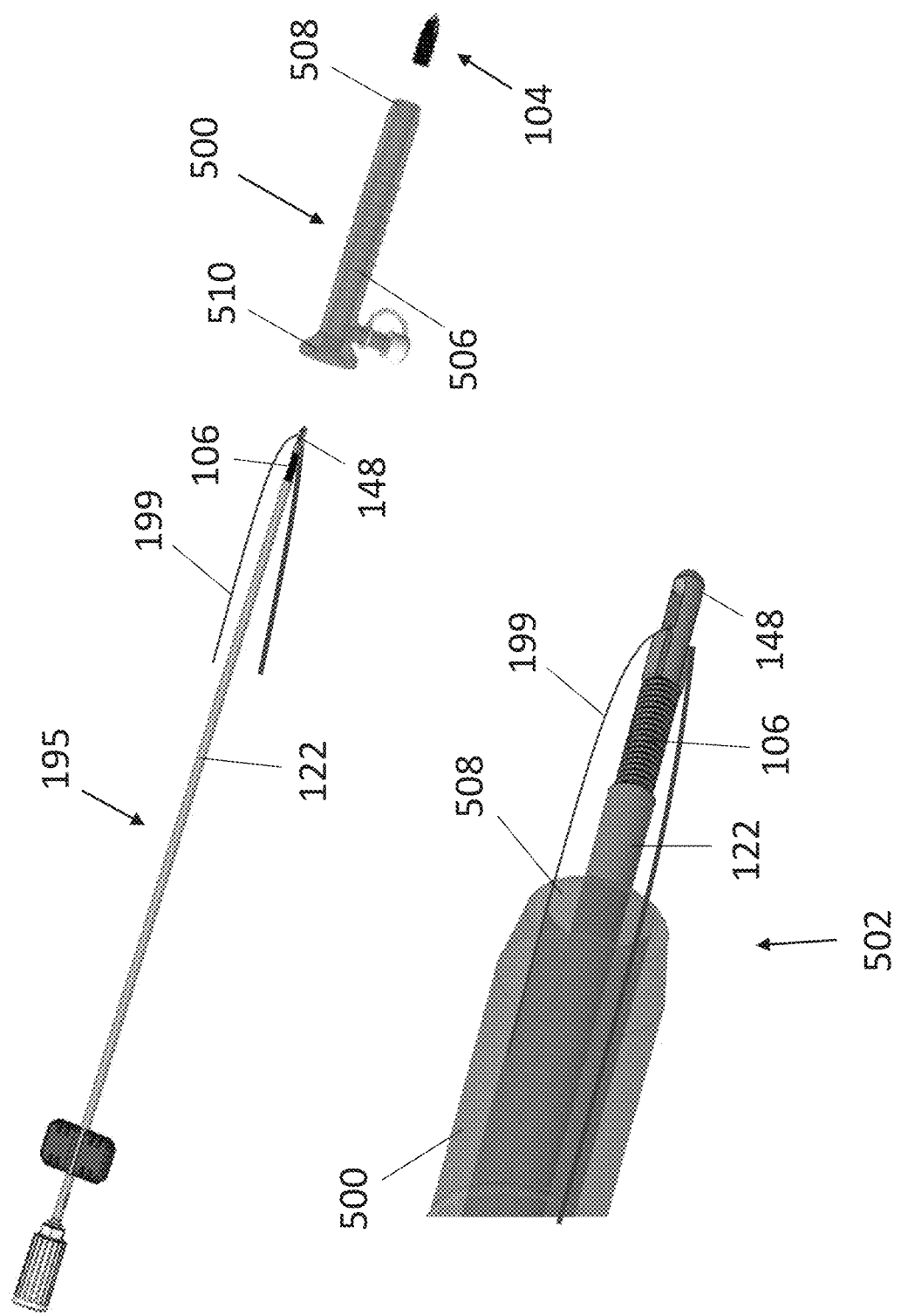

Following the driving of anchor into bone, a length of suture attached to an eyelet shuttle is driven into the anchor to a secured position. Now referring to FIG. 20B, shuttle driver 195 with an attached set screw 106, eyelet shuttle 148 and suture 199 are inserted into proximal opening 510 of drill guide 500. Screw driver 122, set screw 106, eyelet shuttle 148 and suture 199 proceed through cannula 506 of drill guide 500 to exit the distal opening 508 and make contact with anchor 104. Upon rotating torque wrench 130 along the longitudinal axis, screw driver 122 and set screw 106 also rotate, driving eyelet shuttle 148 with suture 199 into a secured position within anchor 104.

Methods of Repairing Soft Tissue to Bone

The present invention also provides methods of repairing soft tissue to bone using the knotless suture anchor devices described herein. In various embodiments, the soft tissue can be a tendon or a ligament. In some embodiments, the methods are useful in securing soft tissue to bone, such as in rotator cuff repair.

Figure 14:
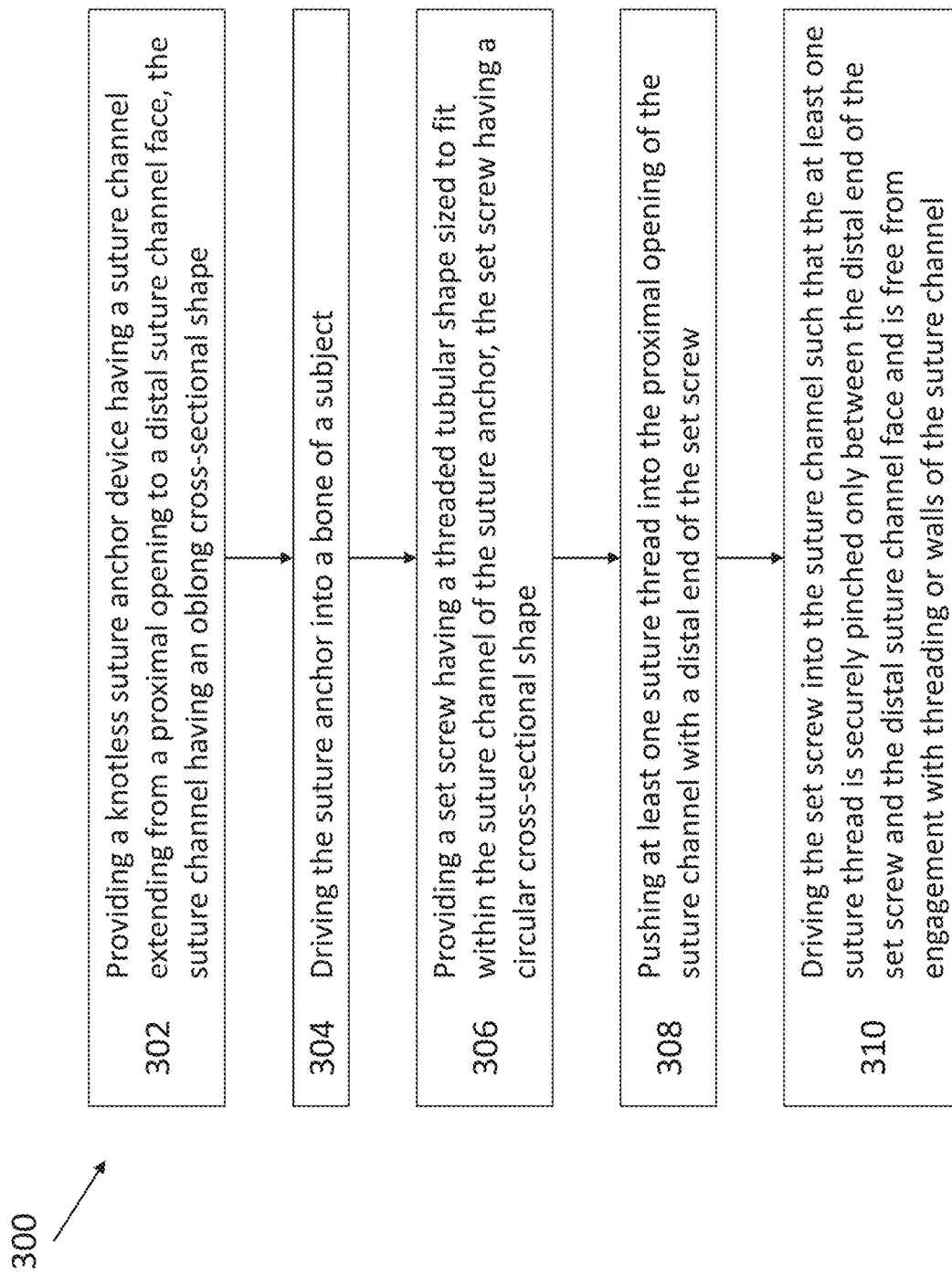
FIG. 14 is a flowchart of an exemplary method of repairing soft tissue to bone.
Figure 15A:
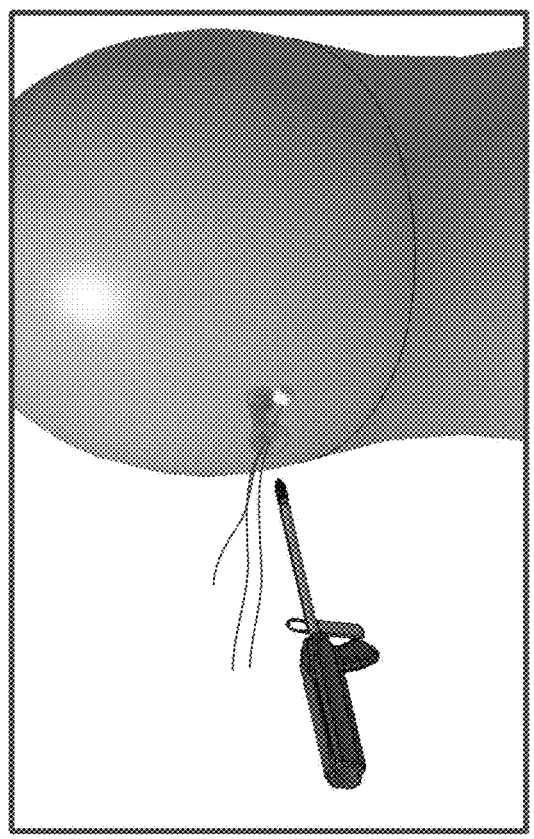
FIG. 15A through FIG. 15F depict a series of images illustrating an exemplar method of repairing soft tissue to bone.
Figure 15B:
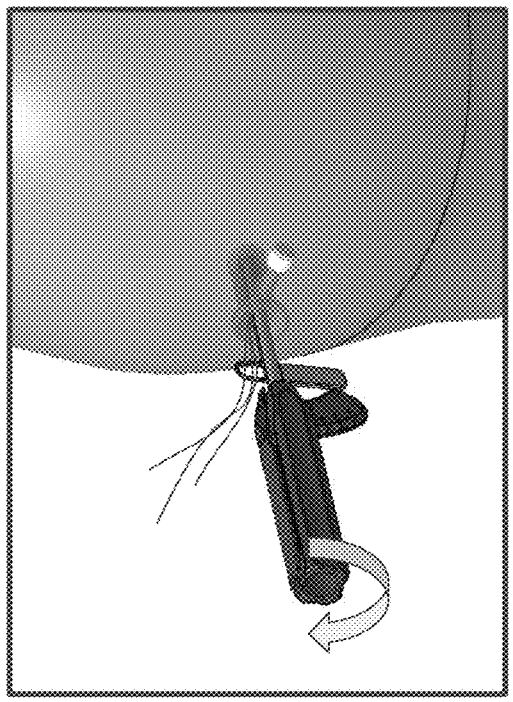
Figure 15D:
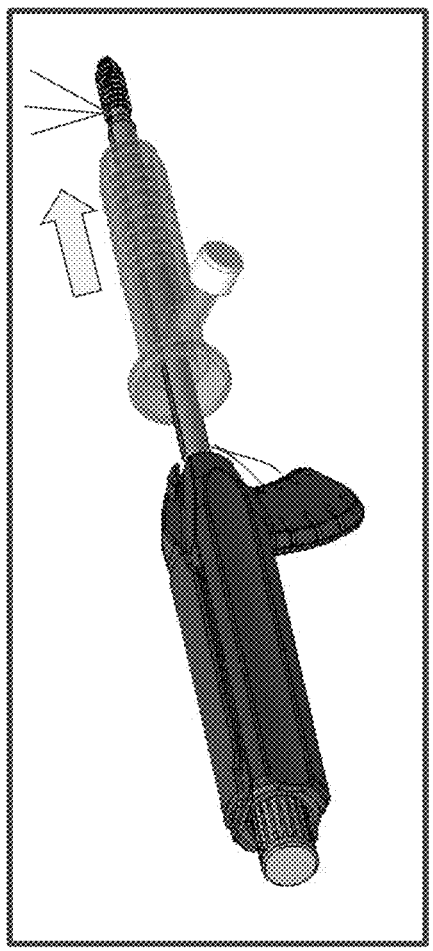
Figure 15C:
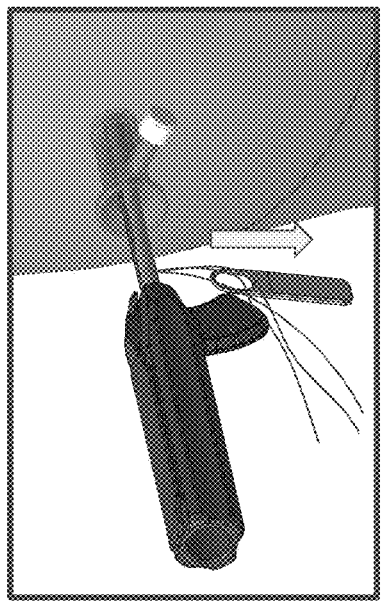
Figure 15F:
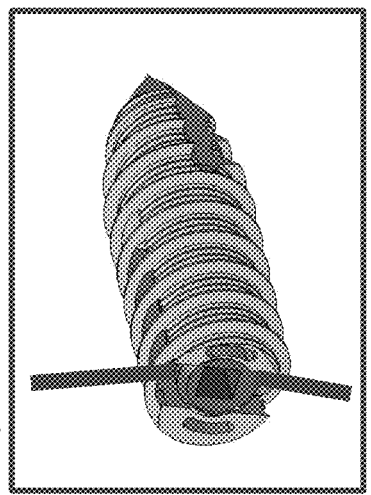
Figure 15E:
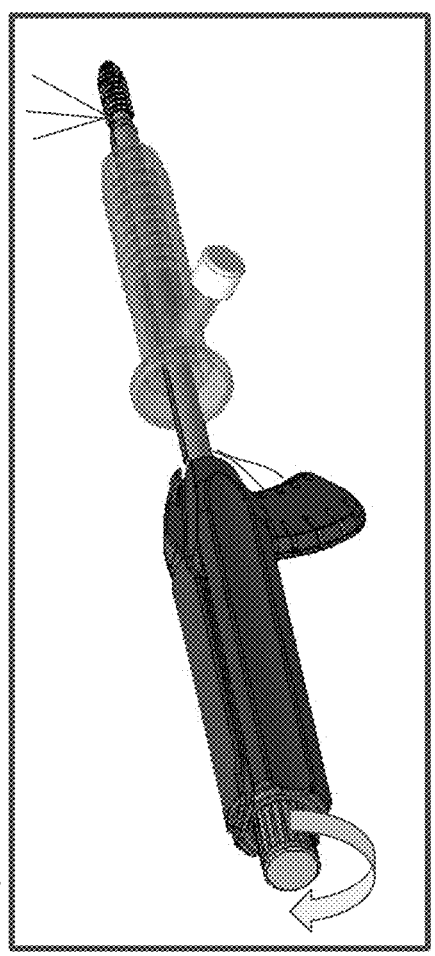

Referring now to FIG. 14, an exemplary method 300 of repairing soft tissue to bone is depicted. The steps of method 300 are visually depicted in FIG. 15A through FIG. 15F. Method 300 begins with step 302 of providing a knotless suture anchor device having a suture channel extending from a proximal opening to a distal suture channel face, the suture channel having an oblong cross-sectional shape (FIG. 15A). In step 304, the suture anchor is driven into a bone of a subject (FIG. 15B). In some embodiments, the suture anchor is driven into a preformed hole in the bone, which may be formed using a tool such as an awl, tap, drill, or the like. In some embodiments, the suture anchor is punched or hammered directly into bone without a preformed hole. In step 306, a set screw is provided having a threaded tubular shape sized to fit within the suture channel of the suture anchor, the set screw having a circular cross-sectional shape. In some embodiments, the set screw can be simultaneously provided with the suture anchor, both being engaged to a suture anchor driver. In step 308, at least one suture thread is pushed into the proximal opening of the suture channel with a distal end of the set screw. FIG. 15C depicts an initial step of passing at least one suture thread into a suture anchor driver such that advancing a set screw towards the suture anchor pushes the at least one suture thread into the proximal opening of the suture channel (FIG. 15D). In step 310, the set screw is driven into the suture channel such that the at least one suture thread is securely pinched only between the distal end of the set screw and the distal suture channel face and is free from engagement with threading or walls of the suture channel (FIG. 15E, FIG. 15F). As described elsewhere herein, the remainder of the at least one suture thread is positioned in lateral spaces of the oblong suture channel adjacent to the set screw.

In some embodiments, the at least one suture thread can be re-tensioned by partially driving the set screw out of the suture channel to free the at least one suture from the distal end of the set screw and the distal suture channel face. After re-tensioning the at least one suture thread, the set screw can be driven back into the suture channel to securely pinch the at least one thread between the distal end of the set screw and the distal suture channel face.

Figure 16:
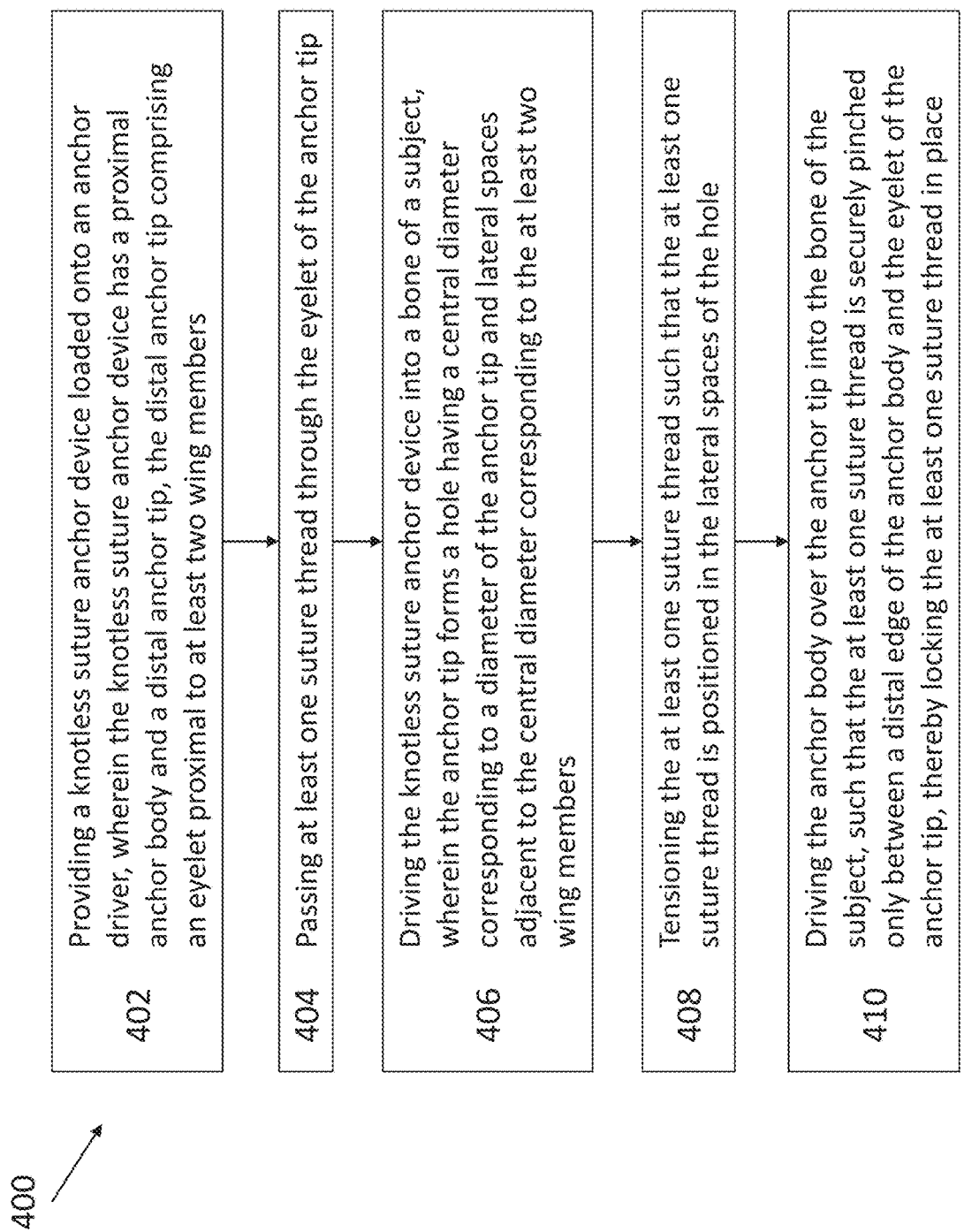
FIG. 16 is a flowchart of an exemplary method of repairing soft tissue to bone.
Figure 17A:
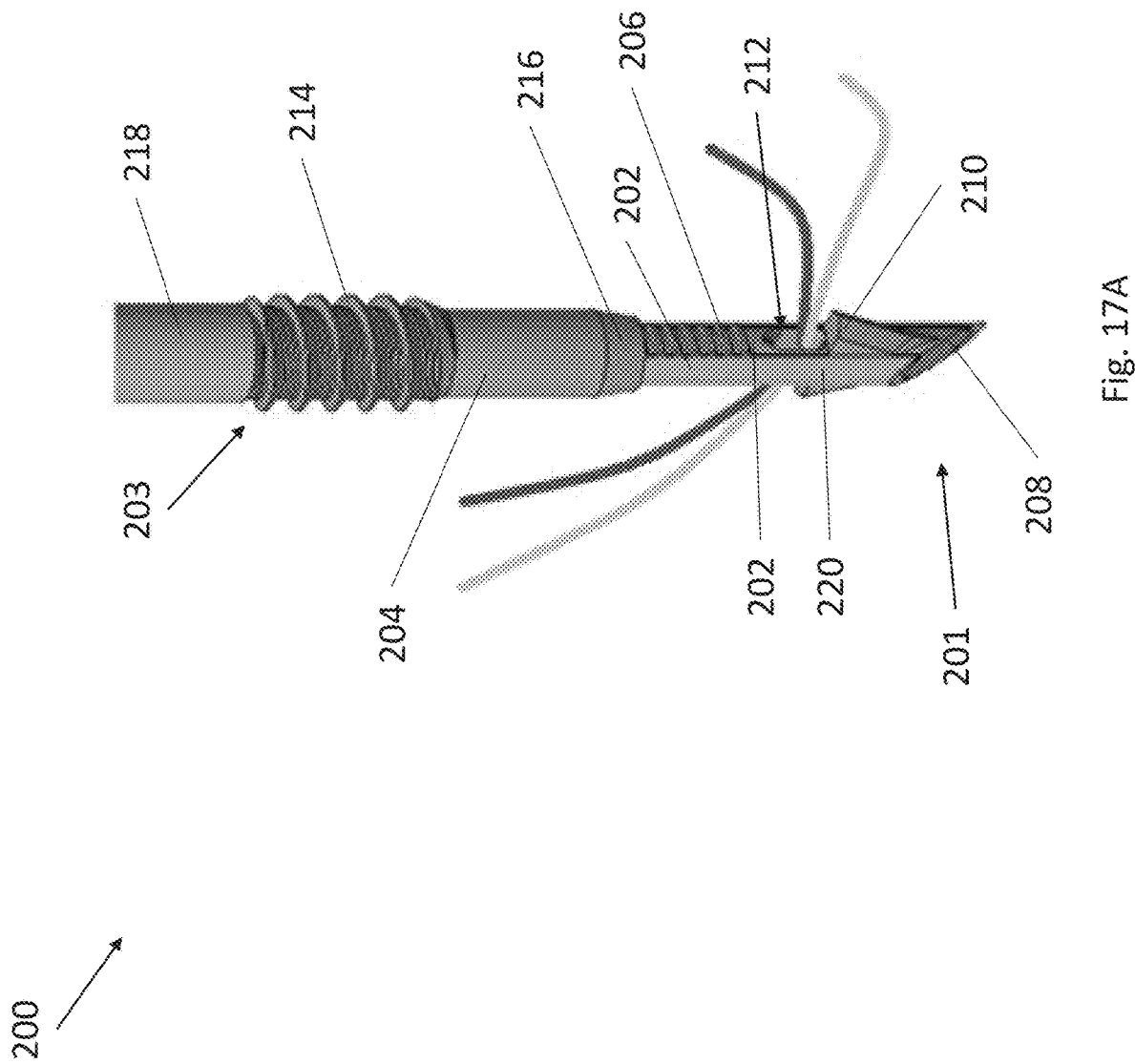
FIG. 17A through FIG. 17D depict a series of images illustrating an exemplary method of repairing soft tissue to bone.
Figure 17D:
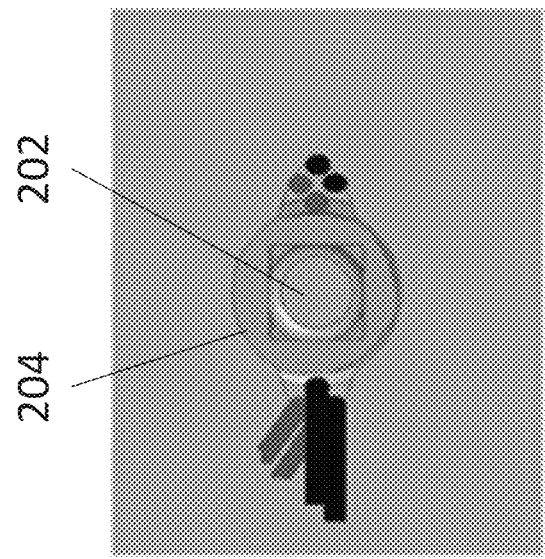
Figure 17C:
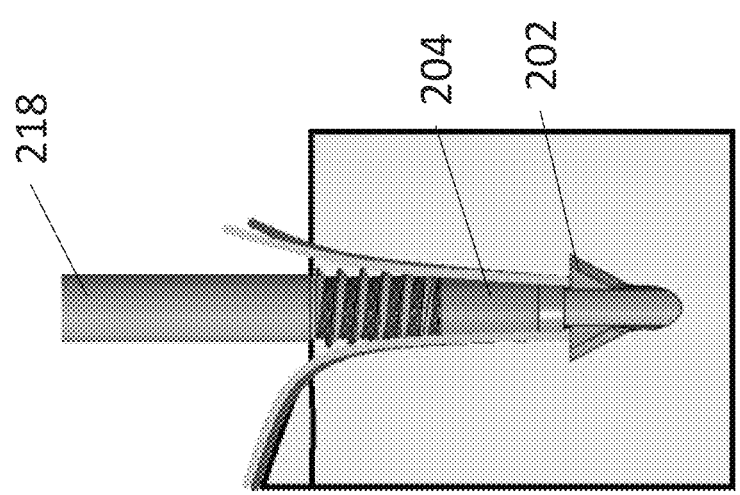
Figure 17B:
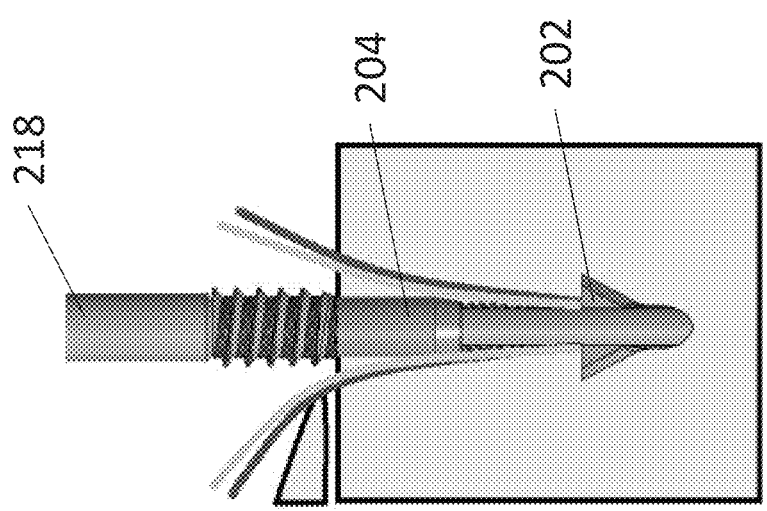

Referring now to FIG. 16, an exemplary method 400 of repairing soft tissue to bone is depicted. The steps of method 400 are visually depicted in FIG. 17A through FIG. 17D. Method 300 begins with step 402 of providing a knotless suture anchor device loaded onto an anchor driver, wherein the knotless suture anchor device has a proximal anchor body and a distal anchor tip, the distal anchor tip comprising an eyelet proximal to at least two wing members. In step 404, at least one suture thread is passed through the eyelet of the anchor tip (FIG. 17A). In step 406, the knotless suture anchor device is driven into a bone of a subject (FIG. 17B), wherein the anchor tip forms a hole having a central diameter corresponding to a diameter of the anchor tip and lateral spaces adjacent to the central diameter corresponding to the at least two wing members. In some embodiments, the knotless suture anchor device is driven into a preformed hole in the bone, which may be formed using a tool such as an awl, tap, drill, or the like. In some embodiments, the knotless suture anchor device is punched or hammered directly into bone without a preformed hole. In step 408, the at least one suture thread is tensioned, such that the at least one suture thread is positioned in the lateral spaces of the hole. In step 410, the anchor body is driven over the anchor tip into the bone of the subject, such that the at least one suture thread is securely pinched only between a distal edge of the anchor body and the eyelet of the anchor tip, thereby locking the at least one suture thread in place (FIG. 17C). As described in step 308, the remainder of the at least one suture thread is positioned in the lateral spaces of the hole and is not engaged between the anchor body or the bone (FIG. 17D).

In some embodiments, the at least one suture thread can be re-tensioned by partially driving the anchor body out of the bone to free the at least one suture from the distal edge of the anchor body and the eyelet of the anchor tip. After re-tensioning the at least one suture thread, the anchor body can be driven back into the bone to securely pinch the at least one thread between the distal edge of the anchor body and the eyelet of the anchor tip.

Figure 18:
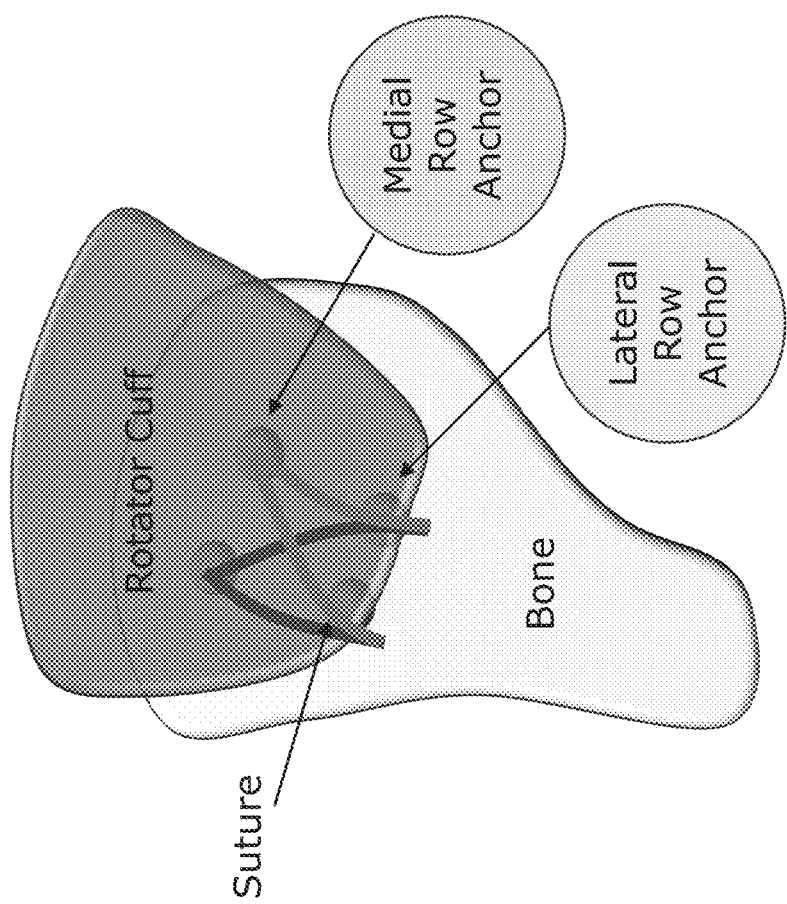
FIG. 18 is a diagram depicting repaired soft tissue to bone using an exemplary method of the present invention.

In some embodiments, the methods of the present invention can be repeated for one or more knotless suture anchor devices for fixation of soft tissue at one or more locations along the bone. The number and spacing of the anchors may be varied depending on the particular application and extent of an injury. In some embodiments, one or more of the knotless suture anchor devices can be implanted into bone to form a medial row of anchors, a lateral row of anchors, or both as would be understood by persons having skill in the art that are versed in rotator cuff repair. Referring now to FIG. 18, the medial row of anchors and the lateral row of anchors are positioned beneath soft tissue (such as a tendon) such that the soft tissue completely covers each of the anchors. The knotless suture anchors of the present invention are particularly advantageous in the application depicted in FIG. 18 by permitting suture threads to be anchored without committing to a fastened position at the time of anchor insertion, such that re-tensioning suture threads may be easily performed once all anchors are in place and can be re-tensioned even at a later time, such as in a post-operative follow up.

Figure 21:
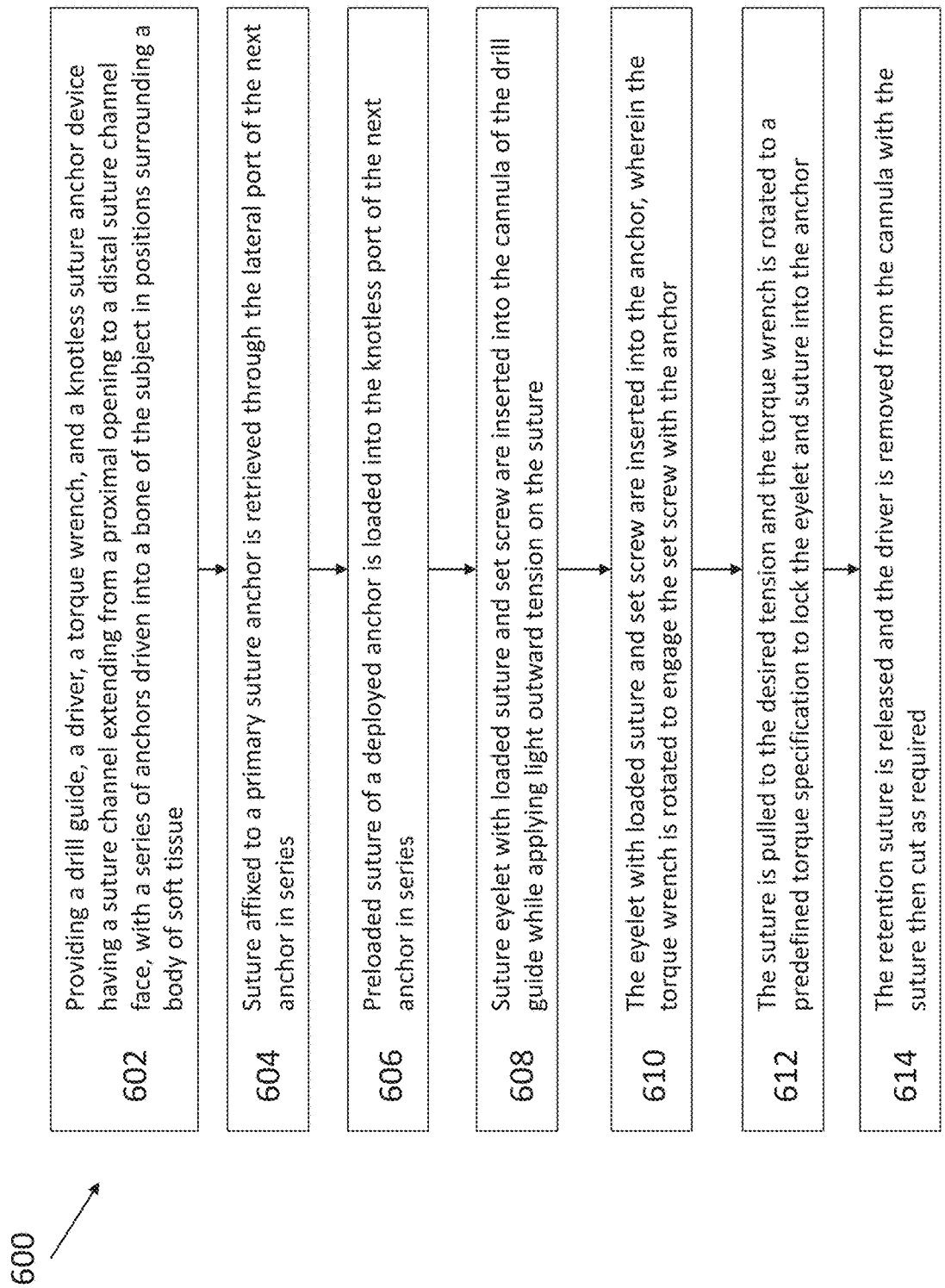
FIG. 21 is a flowchart of an exemplary method of repairing soft tissue to bone.
Figure 22A:
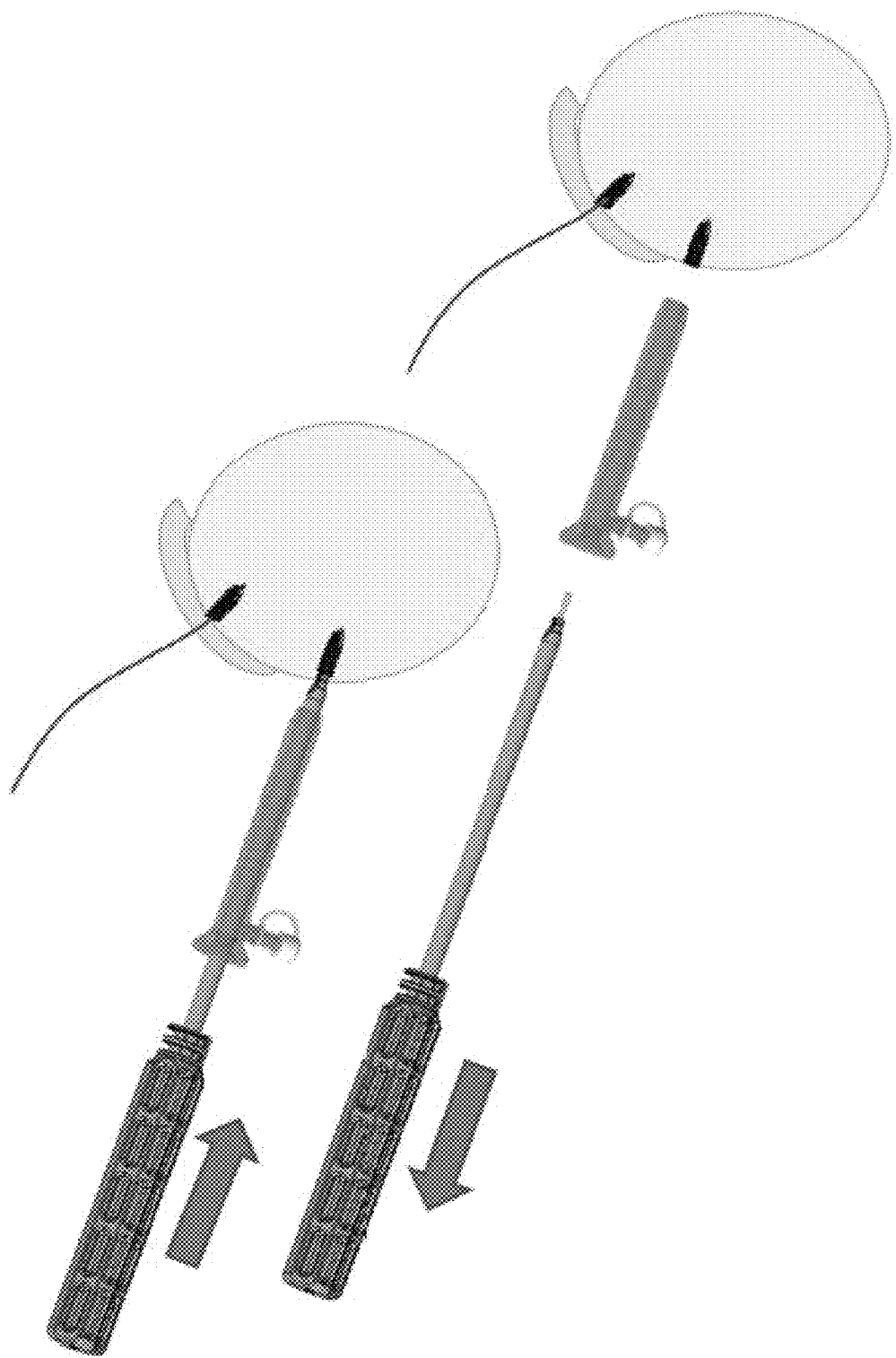
Figure 22B:
Figure 22C:
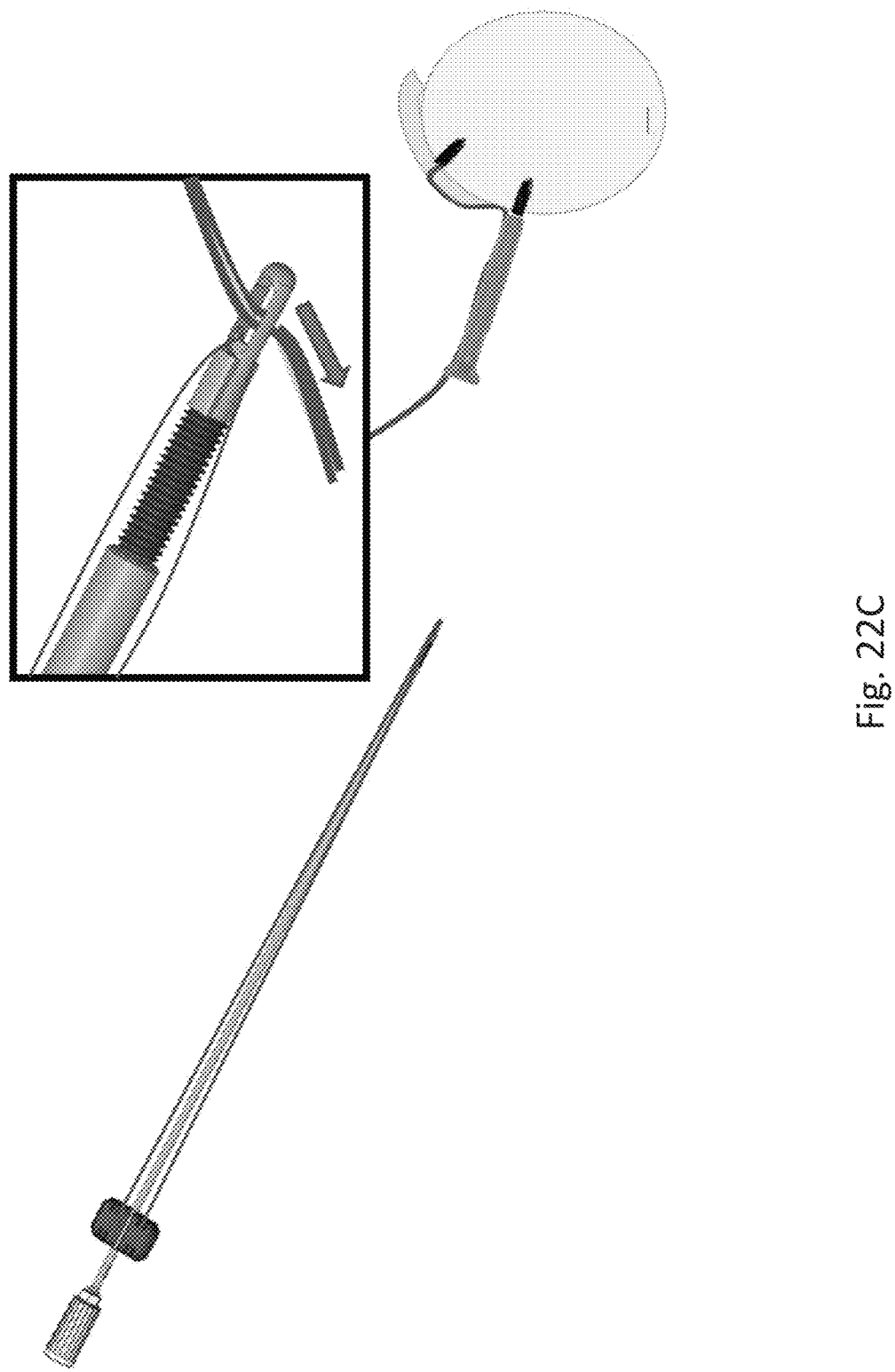
Figure 22D:
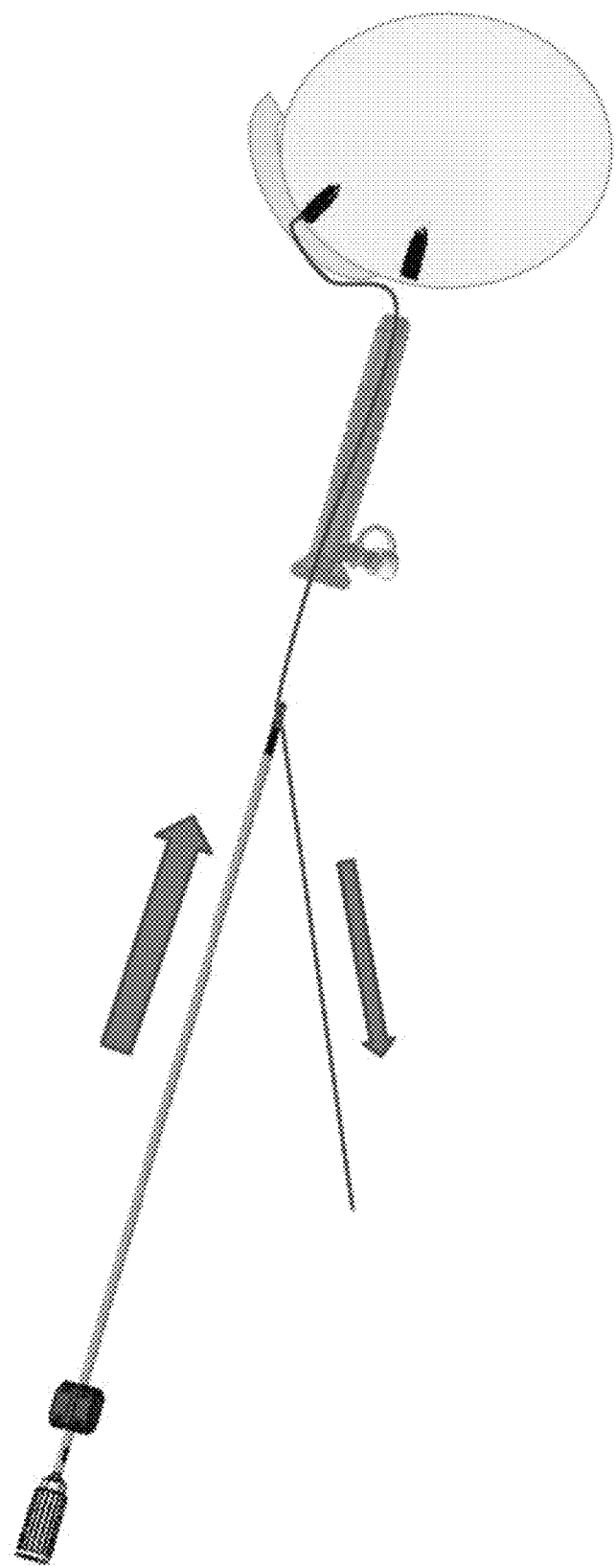
Figure 22E:
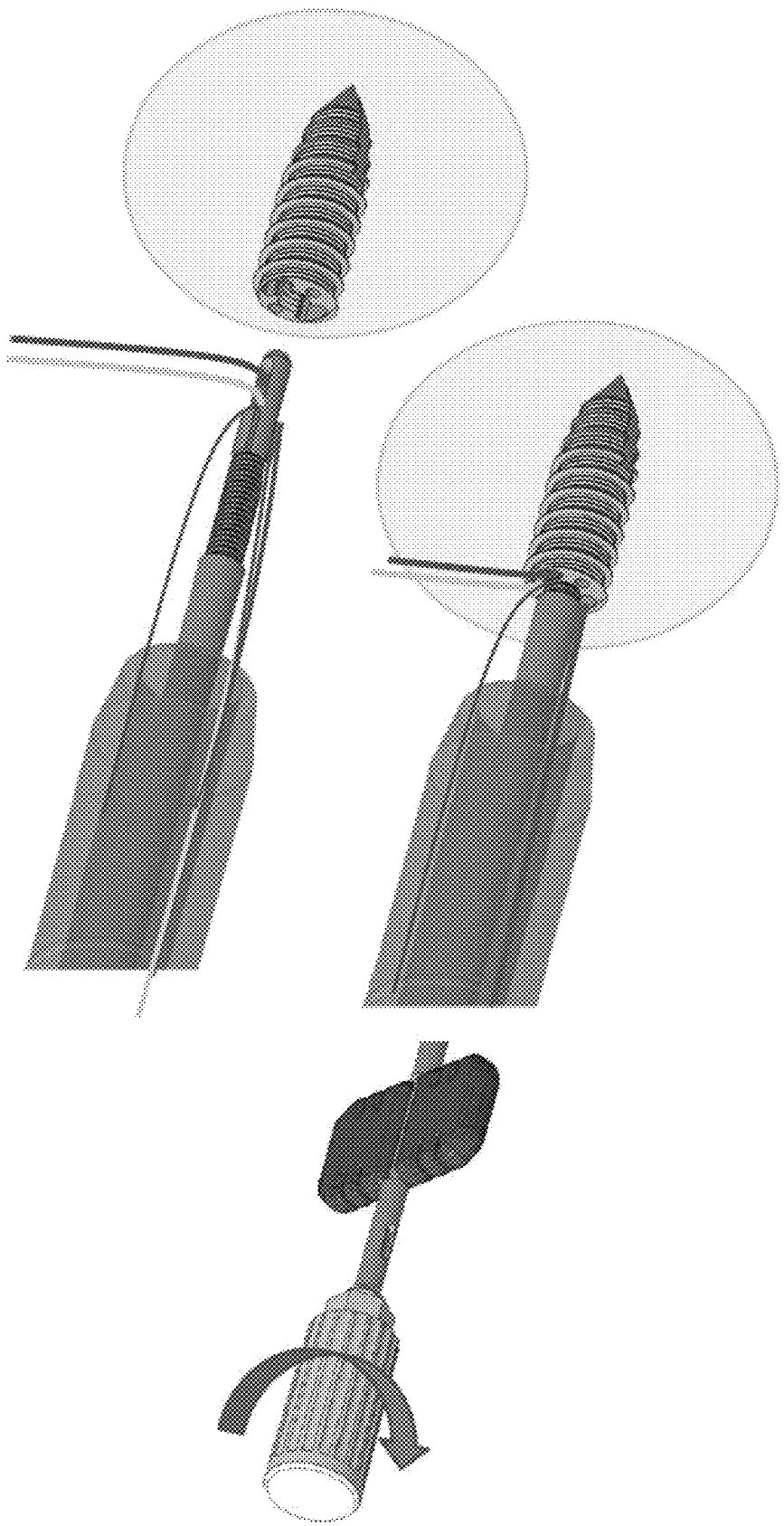
Figure 22F:
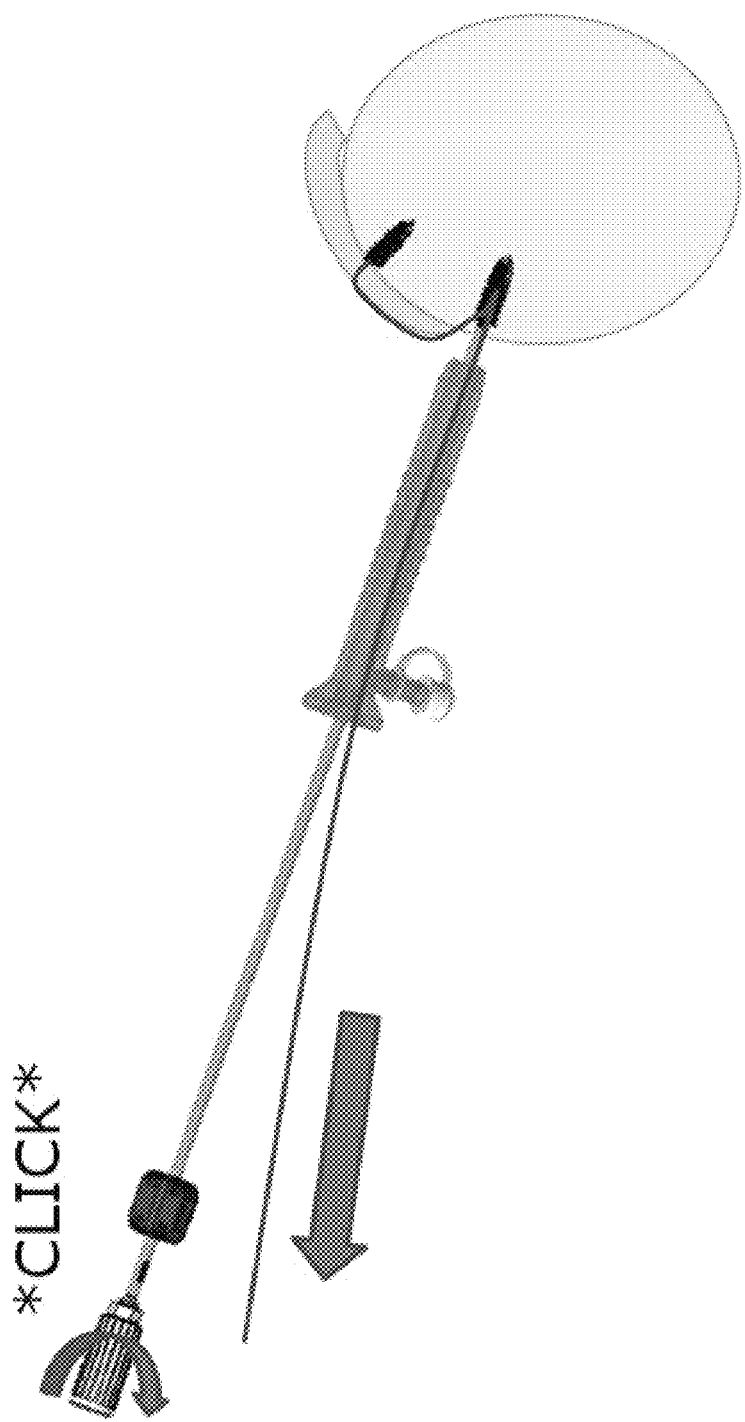

Referring now to FIG. 21, an exemplary method 600 of repairing soft tissue to bone is depicted wherein the anchors are linked by suture in a pattern across a body of soft tissue. The steps of method 600 are visually depicted in FIG. 22A through FIG. 22G. Method 600 begins with step 602 of providing a drill guide, a driver and a knotless suture anchor device having a suture channel extending from the proximal opening to a distal suture channel face, and a series of suture anchors driven into a bone of the subject in positions surrounding a body of soft tissue (FIG. 22A). In some embodiments, the suture anchor is driven into a preformed hole in the bone, which may be formed using a tool such as an awl, tap, drill, or the like. In some embodiments, the suture anchor is punched or hammered directly into bone without a preformed hole. In step 604, the suture affixed to a primary suture anchor is retrieved through the lateral port of the next anchor in series (FIG. 22B). In step 606, the preloaded suture of a deployed anchor is loaded into the knotless port of the next anchor in series (FIG. 22C). In step 608, the suture eyelet with loaded suture and set screw are inserted into the cannula of the drill guide while applying light outward tension on the suture (FIG. 22D). In step 610, the eyelet with loaded suture and set screw are inserted into the anchor, wherein the torque wrench driver is rotated to engage the set screw with the anchor (FIG. 22E). In step 612, the suture is pulled to the desired tension and the torque wrench driver is rotated to a predefined torque specification to lock the eyelet and suture into the anchor (FIG. 22F). In step 614, the retention suture is released and the driver is removed from the cannula with the suture then cut as required (FIG. 22G). As described elsewhere herein, the remainder of the at least one suture thread is positioned in lateral spaces of the oblong suture channel adjacent to the set screw.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A knotless suture anchor device comprising:
a suture anchor comprising an elongate cylindrical body having a proximal end and a distal end, and a suture channel extending from an opening at the proximal end to a distal suture channel face, wherein the suture channel comprises an oblong cross-sectional shape; and
a set screw comprising an elongate tubular body having a proximal end and a distal end, a screw thread positioned on an outer surface of the tubular body, wherein the set screw is configured to screw into the suture channel to form opposing lateral spaces in the suture channel.

2. The device of claim 1, wherein the set screw and the suture anchor are configured to reversibly fasten one or more lengths of suture thread within the suture channel such that the one or more lengths of suture thread are pinched only between the distal end of the set screw and the distal suture channel face while remaining free from engagement with threading or walls of the suture channel.

3. The device of claim 1, wherein the suture channel comprises opposing partial threading mated to the screw thread of the set screw.

4. The device of claim 1, wherein the suture anchor comprises a distal piercing tip having a shape selected from the group consisting of: a conical tip, a pyramidal tip, a hypodermic needle tip, a wedge tip, a bladed tip, and a trocar tip.

5. The device of claim 1, wherein the suture anchor is fabricated from a material selected from the group consisting of: PEEK, PAEK, PEKK, titanium, titanium-alloys, bioabsorbables, platinum, plastic, metal, and combinations thereof.

6. The device of claim 1, wherein the suture anchor is engageable to a distal end of an outer driver of an anchor driver and the set screw is engageable to a distal end of an inner set screw driver of the anchor driver positioned within a lumen of the outer driver.

7. The device of claim 6, wherein the outer driver and the inner set screw driver each rotate about a longitudinal axis of the anchor driver, and the inner set screw driver rotates independently from the outer driver.

8. The device of claim 6, wherein the inner set screw driver is rotatably connected to and telescopes from a drive shaft that is rotatably connected to a proximal end of the anchor driver.

9. The device of claim 6, wherein the outer driver comprises opposing longitudinal suture slots configured to receive one or more lengths of suture thread.

10. The device of claim 9, wherein the outer driver further comprises a releasably engaged suture blocking sleeve comprising a tube-like shape having a central lumen with an open lateral side, such that the suture blocking sleeve is rotatable to cover and expose one or more of the opposing longitudinal suture slots.

11. The device of claim 9, wherein the inner set screw driver is configured to push one or more lengths of suture thread received through the opposing longitudinal suture slots into the suture anchor.

12. The device of claim 1, wherein the anchor device further comprises a substantially cylindrical eyelet shuttle having an eyelet configured to receive a suture therethrough, wherein the eyelet shuttle is configured to fit within a shuttle slot formed within the distal suture channel face.

13. The device of claim 12, wherein the eyelet shuttle comprises an interference rib extending from a proximal end of the eyelet in a distal direction.

14. The device of claim 12, wherein the eyelet shuttle comprises laterally extending proximal tabs configured to reversibly fasten one or more lengths of suture thread within the suture channel such that the one or more lengths of suture thread are pinched only between the proximal tabs and the distal suture channel face while remaining free from engagement with threading or walls of the suture channel.

15. The device of claim 14, wherein the distal suture channel face comprises a tab slot formed adjacent to the shuttle slot configured to reversibly fasten one or more lengths of suture thread within the suture channel such that the one or more lengths of suture thread are pinched only between the proximal tabs and distal and lateral faces of the tab slot while remaining free from engagement with threading or walls of the suture channel.

16. The device of claim 1, wherein the suture anchor comprises a threaded exterior.

17. The device of claim 1, wherein the suture anchor comprises a ribbed exterior configured for push-in insertion.

18. The device of claim 1, wherein the suture anchor comprises an exterior having a plurality of flexing flaps configured for push-in insertion, wherein each flexing flap extends out of the cylindrical body and is angled towards the proximal end of the cylindrical body.

19. The device of claim 1, wherein the suture anchor comprises one or more flexible ribs having a retracted position and an extended position, wherein in the retracted position the one or more flexible ribs are withdrawn into the cylindrical body and at least partially abut into the suture channel, and upon screwing in the set screw the one or more flexible ribs extend out of the cylindrical body into the extended position.

20. A method of attaching soft tissue to bone, the method comprising the steps of:
providing a knotless suture anchor device having a suture channel extending from a proximal opening to a distal suture channel face, the suture channel having an oblong cross-sectional shape;
driving the suture anchor into a bone of a subject;
providing a set screw having a threaded tubular shape sized to fit within the suture channel of the suture anchor, the set screw having a circular cross-sectional shape;
pushing at least one suture thread into the proximal opening of the suture channel with a distal end of the set screw; and
driving the set screw into the suture channel such that the at least one suture thread is securely pinched only between the distal end of the set screw and the distal suture channel face and is free from engagement with threading or walls of the suture channel.

21. The method of claim 20, wherein the knotless suture anchor is driven into a preformed hole in a bone of a subject.

22. The method of claim 21, wherein the hole is formed using a tool selected from the group consisting of: an awl, a tap, and a drill.

23. The method of claim 20, wherein the knotless suture anchor is punched or hammered directly into a bone of a subject without a preformed hole.

24. The method of claim 20, wherein the at least one suture thread is re-tensioned by partially driving the set screw out of the suture channel to free the at least one suture from the distal end of the set screw and the distal suture channel face.

25. The method of claim 20, wherein a remainder of each of the at least one suture thread is positioned in lateral spaces of the suture channel adjacent to the set screw.

26. A knotless suture anchor device comprising:
an anchor tip comprising an elongate cylindrical body having a proximal end and a distal end, an eyelet, a distal piercing tip, and at least two wing members extending laterally from the cylindrical body distal to the eyelet; and
an anchor body comprising an elongate tubular body having a proximal end and a distal end, a screw thread positioned on an outer surface of the tubular body, and an inner lumen sized to fit the cylindrical body of the anchor tip.

27. The device of claim 26, wherein the anchor tip comprises a screw thread extending from the distal end of the cylindrical body towards the eyelet.

28. The device of claim 27, wherein the anchor body comprises a screw thread positioned on an inner surface of the inner lumen mated to the screw thread of the anchor tip.

29. The device of claim 26, wherein the at least two wing members each comprise a proximally facing surface and taper towards the piercing tip.

30. The device of claim 26, wherein the piercing tip has a shape selected from the group consisting of: a conical tip, a pyramidal tip, a hypodermic needle tip, a wedge tip, a bladed tip, and a trocar tip.

31. The device of claim 26, wherein the anchor member is fabricated from a material selected from the group consisting of: PEEK, PAEK, PEKK, titanium, titanium-alloys, bioabsorbables, platinum, plastic, metal, and combinations thereof.

32. The device of claim 26, wherein the eyelet is formed from a lumen passing through the cylindrical body from a first lateral opening to an opposing second lateral opening, such that the eyelet can accept at least one suture thread.

33. The device of claim 26, wherein tubular body of the anchor body has a diameter that is larger than a diameter of the cylindrical body of the anchor tip and is smaller than a lateral extension of each of the at least two wing members.

34. The device of claim 26, wherein the anchor body is engageable to an outer driver of an anchor driver and the anchor tip is engageable to an inner driver of the anchor driver.

35. The device of claim 34, wherein the outer driver rotates independently from the inner driver.

36. The device of claim 34, wherein the inner driver comprises one or more tines that extend through the anchor body, past the anchor tip, and terminate in a penetrating tip complementing the piercing tip of the anchor tip.

37. The device of claim 34, wherein the anchor driver is made from a metal and the anchor body and the anchor tip are each metal-free.

38. The device of claim 26, wherein the anchor tip has a length between about 5 mm to about 50 mm and a diameter between about 5 mm to about 15 mm.

39. The device of claim 26, wherein the anchor body has a length between about 5 mm to about 50 mm and a diameter between about 5 mm to about 20 mm.

40. A method of attaching soft tissue to bone, the method comprising the steps of:
providing the knotless suture anchor of claim 22 loaded onto an anchor driver;
passing at least one suture thread through the eyelet of the anchor tip;
driving the knotless suture anchor device into a bone of a subject, wherein the anchor tip forms a hole having a central diameter corresponding to a diameter of the anchor tip and lateral spaces adjacent to the central diameter corresponding to the at least two wing members;

tensioning the at least one suture thread such that the at least one suture thread is positioned in the lateral spaces of the hole; and driving the anchor body over the anchor tip into the bone of the subject, such that the at least one suture thread is securely pinched only between a distal edge of the anchor body and the eyelet of the anchor tip, thereby locking the at least one suture thread in place.

41. The method of claim 40, wherein the knotless suture anchor is driven into a preformed hole in a bone of a subject.

42. The method of claim 41, wherein the hole is formed using a tool selected from the group consisting of: an awl, a tap, and a drill.

43. The method of claim 40, wherein the knotless suture anchor is punched or hammered directly into a bone of a subject without a preformed hole.

44. The method of claim 40, wherein the at least one suture thread is re-tensioned by partially driving the anchor body out of the bone to free the at least one suture from the distal edge of the anchor body and the eyelet of the anchor tip.

45. The method of claim 40, wherein a remainder of each of the at least one suture thread is positioned in the lateral spaces of the hole and is not engaged between the anchor body and the bone.

46. A method of attaching soft tissue to bone, the method comprising the steps of:

Providing a drill guide, a driver, a torque wrench and a knotless suture anchor of any preceding claim loaded on to the driver;

a series of anchors are driven into a bone of a subject in positions surrounding a body of soft tissue;

the suture affixed to a primary suture anchor is retrieved through the lateral port of the next anchor in series;

the suture affixed to the primary suture anchor is passed through the suture eyelet of the next anchor in series;

the suture eyelet with loaded suture and set screw are inserted into the cannula of the drill guide while applying outward tension on the suture;

the eyelet with loaded suture and set screw are inserted into the anchor, wherein the torque wrench is rotated to engage the set screw with the anchor;

the suture is pulled to the desired tension and the torque wrench is rotated to a predefined torque specification to lock the eyelet and suture into the anchor;

the retention suture is released and the driver is removed from the cannula with the suture then cut as required.

* * * * *